United States Patent
Reuter et al.

(10) Patent No.: US 11,760,712 B2
(45) Date of Patent: Sep. 19, 2023

(54) TRIARYLMETHANE COMPOUNDS

(71) Applicant: MITSUBISHI GAS CHEMICAL COMPANY, INC., Tokyo (JP)

(72) Inventors: Karl Reuter, Freiburg (DE); Vasyl Andrushko, Freiburg (DE); Mark Kantor, Freiburg (DE); Florian Stolz, Freiburg (DE); Munenori Shiratake, Ibaraki (JP); Kentaro Ishihara, Tokyo (JP); Koji Hirose, Tokyo (JP); Shinya Ikeda, Tokyo (JP); Noriyuki Kato, Tokyo (JP); Mitsuteru Kondo, Tokyo (JP); Shoko Murata, Tokyo (JP); Kensuke Oshima, Tokyo (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 65 days.

(21) Appl. No.: 16/968,106

(22) PCT Filed: Feb. 1, 2019

(86) PCT No.: PCT/EP2019/052506
§ 371 (c)(1),
(2) Date: Aug. 6, 2020

(87) PCT Pub. No.: WO2019/154730
PCT Pub. Date: Aug. 15, 2019

(65) Prior Publication Data
US 2021/0371367 A1  Dec. 2, 2021

(30) Foreign Application Priority Data
Feb. 9, 2018  (EP) .................................... 18156161

(51) Int. Cl.
*C07C 43/23* (2006.01)
*C08G 64/06* (2006.01)
(Continued)

(52) U.S. Cl.
CPC ............ *C07C 43/23* (2013.01); *C08G 63/193* (2013.01); *C08G 64/06* (2013.01); *C08G 64/305* (2013.01); *G02B 1/04* (2013.01); *G02B 1/041* (2013.01); *C07C 2602/26* (2017.05); *C07C 2603/18* (2017.05); *C07C 2603/26* (2017.05); *C08L 69/00* (2013.01); *C08L 2203/16* (2013.01)

(58) Field of Classification Search
CPC . C07C 43/23; C07C 2602/26; C07C 2603/18; C07C 2603/26; C07C 255/00; C07C 43/295; C08G 63/193; C08G 64/06; C08G 64/305; C08G 63/195; G02B 1/04; G02B 1/41; G02B 1/041; C08L 69/00; C08L 2203/16; C07D 307/91
USPC ........................................................ 524/534
See application file for complete search history.

(56) References Cited

U.S. PATENT DOCUMENTS

2014/0248561 A1* 9/2014 Echigo ................. C07D 311/96
549/382

FOREIGN PATENT DOCUMENTS

CN    101467073 A    6/2009
CN    103257376 A    8/2013
(Continued)

OTHER PUBLICATIONS

WO 2018016615 A1, machine translation, EPO espacenet. (Year: 2018).*
(Continued)

*Primary Examiner* — Frances Tischler
(74) *Attorney, Agent, or Firm* — Viksnins Harris Padys Malen LLP

(57) ABSTRACT

The present invention relates to triarylmethane compounds of the formula (I), which suitable as monomers for preparing thermoplastic resins having beneficial optical properties and which can be used for producing optical devices. $R^1$, $R^2$ are e.g. hydrogen; Y is an alkylene group having 2, 3 or 4 carbon atoms, Ar is selected from mono- or polycyclic aryl and mono- or polycyclic hetaryl; $X^1$, $X^2$, $X^3$, $X^4$ are CH, C—$R^x$ or N, provided that in each ring at most two of $X^1$, $X^2$, $X^3$, $X^4$ are N; $R^x$ is e.g. halogen, CN or CH=$CH_2$. The invention also relates to thermoplastic resins comprising a polymerized unit of the compound of formula (I).

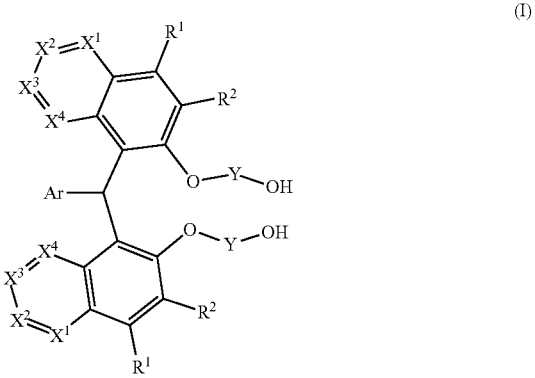

6 Claims, No Drawings

(51) Int. Cl.
*C08G 64/30* (2006.01)
*G02B 1/04* (2006.01)
*C08G 63/193* (2006.01)
*C08L 69/00* (2006.01)

(56) References Cited

FOREIGN PATENT DOCUMENTS

| | | |
|---|---|---|
| CN | 104211585 A | 12/2014 |
| CN | 104769007 A | 7/2015 |
| EP | 2034337 A1 | 3/2009 |
| EP | 2808317 A1 | 12/2014 |
| EP | 2918621 A1 | 9/2015 |
| JP | 2019077672 A | 5/2019 |
| TW | 201321891 A | 6/2013 |
| TW | 201817699 A | 5/2018 |
| TW | 201930242 A | 8/2019 |
| WO | 2018016615 A1 | 1/2018 |
| WO | 2019082541 A1 | 5/2019 |

OTHER PUBLICATIONS

EP Office Action, for EP Application No. 19703970.4, 6 pages, dated Sep. 30, 2021.
EP Office Action, for EP Application No. 19703970.4, 5 pages, dated Mar. 1, 2021.
Patent Cooperation Treaty, International Search Report and Written Opinion for PCT/EP2019/052506, 8 pages, dated Mar. 20, 2019.
Chinese Office Action for CN Application No. 201980012424.0, 17 pages, dated Jun. 13, 2022. [with English Translation].
European Office Action for EP19703970.4, 6 pages, dated May 27, 2022.

* cited by examiner

TRIARYLMETHANE COMPOUNDS

CROSS-REFERENCE TO RELATED APPLICATION

This application claims priority to European Application No. 18156161.4, filed on Feb. 9, 2018.

The present invention relates to triarylmethane compounds that are suitable as monomers for preparing thermoplastic resins, such as polycarbonate resins, which have beneficial optical properties and can be used for producing optical devices.

BACKGROUND OF INVENTION

Optical glass or optical resins are frequently used as a material for an optical lens in optical systems of any of various types of cameras such as a camera, a camera having a film integrated therewith, a video camera and the like. While optical glass is beneficial in heat resistance, transparency, size stability, chemical resistance and the like, its material costs are high. Moreover the moldability is low and thus mass production is difficult.

Optical devices, such as optical lenses, made of optical resin instead of optical glass are advantageous in that they can be produced in large numbers by injection molding. Nowadays, optical resins, in particular, transparent polycarbonate resins, are frequently used for producing camera lenses. In this regard, resins with a higher refractive index are highly desirable, as they allow for reducing the size and weight of final products. In general, when using an optical material with a higher refractive index, a lens element of the same refractive power can be achieved with a surface having less curvature, so that the amount of aberration generated on this surface can be reduced. As a result, it is possible to reduce the number of lenses, to reduce the eccentric sensitivity of lenses and/or to reduce the lens thickness to thereby achieve weight reduction.

In an optical system of a camera, the aberration correction is usually performed by a combination of a plurality of concave and convex lenses. More specifically, a convex lens having a color aberration is combined with a concave lens having a color aberration of an opposite sign to that of the convex lens, so that the color aberration of the convex lens is synthetically cancelled. In this case it is required that the concave lens is highly dispersive, i.e. it must have a low Abbe number.

EP2034337 describes a copolycarbonate resin which comprises 99 to 51 mol % of a repeating unit derived from 9,9-bis(4-(2-hydroxyethoxy)phenyl)fluorene and 1 to 49 mol % of a repeating unit derived from bisphenol A. The resin is suitable for preparing an optical lens having a low Abbe number of 23 to 26 and a refractive index from 1.62 to 1.64.

JP H06-25398 discloses a copolycarbonate resin including a repeating unit derived from 9,9-bis(4-hydroxyphenyl) fluorene and a repeating unit derived from bisphenol A. In an example of this document, it is described that the refractive index reaches 1.616 to 1.636.

U.S. Pat. No. 9,360,593 describes polycarbonate resins having repeating units derived from binaphthyl monomers of the formula (A):

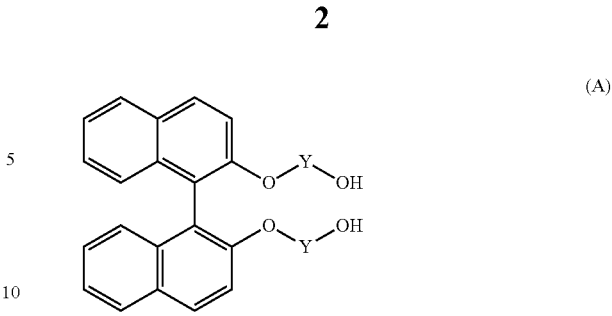

where Y is $C_1$-$C_4$-alkandiyl, in particular 1,2-ethandiyl. It is said that the polycarbonate resins have beneficial optical properties in terms of a high refractive index, a low Abbe's number, a high degree of transparency, low birefringence, and a glass transition temperature suitable for injection molding.

Co-Polycarbonates of monomers of the formula A with 10,10-bis(4-hydroxyphenyl)-anthrone monomers and their use for preparing optical lenses are described in US 2016/0319069. The copolycarbonates are reported to have a good moisture resistance. Refractive indices of about 1.662 to 1.667 have been reported. However, the thermoplastic processability, such as moldability, of the resins is poor.

So far, thermoplastic resin, such as a polycarbonate resins having a high refractive index and a low Abbe number and good thermoplastic processability have not been provided yet. Moreover, various electronic devices should have high moisture resistance and heat resistance. A "PCT test" (pressure cooker test) has been established to evaluate the moisture resistance and the heat resistance of such electronic devices. In this test, penetration of moisture into a sample is increased for a certain time period to evaluate the moisture resistance and the heat resistance. Therefore, an optical lens formed of an optical resin useable for an electronic device needs to have a high refractive index and a low Abbe number, and is also required to maintain high optical properties even after the PCT test.

Despite the advances made in the field of optical resins, here is still an ongoing need for monomers for preparing optical resins, in particular polycarbonate resins, which monomers result in a high refractive index. Apart from that, the monomers should not impair the other optical properties of the optical resins, and should provide at least one of the following properties, namely low Abbe's number, a high degree of transparency and low birefringence. Moreover, the monomers should be easy to prepare. The resins obtained from these monomers should have also a good moisture and heat resistance and they should have a glass transition temperature suitable for injection molding. In particular, they should have a good thermoplastic processability, such as moldability.

SUMMARY OF INVENTION

It was surprisingly found that compounds of the formula (I) as described herein are suitable for preparing optical resins of high transparency and high refractive index. In particular, when used as monomers in the preparation of optical resins, compounds of the formula (I) result in higher refractive indices than the monomers of formula (A).

Therefore, the present invention relates to compounds of the formula (I)

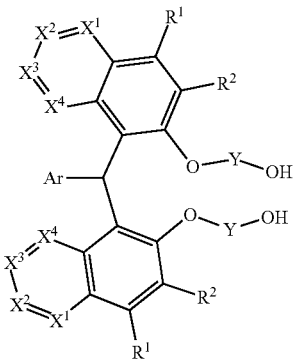

where
- $R^1$, $R^2$ are hydrogen, a radical $R^a$ or $R^1$ and $R^2$ together with the carbon atoms to which they are bound may also form a fused benzene ring, which is unsubstituted or substituted by one radical $R^a$,
- Y represents an alkylene group having 2, 3 or 4 carbon atoms,
- Ar is selected from the group consisting of mono- or polycyclic aryl having from 6 to 26 carbon atoms and mono- or polycyclic hetaryl having a total of 5 to 26 atoms, which are ring members, where 1, 2, 3 or 4 of these atoms are selected from nitrogen, sulphur and oxygen, while the remainder of these atoms are carbon atoms, where mono- or polycyclic aryl and mono- or polycyclic hetaryl are unsubstituted or carry 1, 23 or 4 radicals $R^{Ar}$;
- $X^1$, $X^2$, $X^3$, $X^4$ are CH, C—$R^x$ or N, provided that in each ring at most two of $X^1$, $X^2$, $X^3$, $X^4$ are N;
- $R^a$ is selected from the group consisting of fluorine, cyclopropyl, cyclobutyl, CN, R, OR, $CH_nR_{3-n}$, $NR_2$, C(O)R, C(O)$NH_2$, CH=$CH_2$, CH=CHR, $CH_2$—CH=$CH_2$, $CH_2$—CH=CHR', $CH_2$—C≡CH and $CH_2$—C≡CR';
- $R^{Ar}$ is selected from the group consisting of fluorine, cyclopropyl, cyclobutyl, CN, R, OR, $CH_nR_{3-n}$, $NR_2$, C(O)R, C(O)$NH_2$, CH=$CH_2$, CH=CHR', $CH_2$—CH=$CH_2$, $CH_2$—CH=CHR', $CH_2$—C≡CH and $CH_2$—C≡CR', it being possible that $R^{Ar}$ is identical or different if more than 1 is present on each ring;
- $R^x$ is selected from the group consisting of halogen, cyclopropyl, cyclobutyl, CN, R, OR, $CH_nR_{3-n}$, $NR_2$, C(O)R, CH=$CH_2$, CH=CHR', $CH_2$—CH=$CH_2$, $CH_2$—CH=CHR', $CH_2$—C≡CH and $CH_2$—C≡CR', it being possible that $R^x$ is identical or different if more than 1 is present on each ring;
- R is selected from methyl, mono or polycyclic aryl having from 6 to 26 carbon atoms and mono- or polycyclic hetaryl having a total of 5 to 26 atoms, which are ring members, where 1, 2, 3 or 4 of the ring atoms of hetaryl are selected from nitrogen and oxygen, while the remainder of these atoms are carbon atoms, where mono- or polycyclic aryl are unsubstituted or substituted by 1, 2, 3 or 4 identical or different radicals R";
- R' is selected from methyl, mono- or polycyclic aryl having from 6 to 26 carbon atoms and mono- or polycyclic hetaryl having a total of 5 to 26 atoms, which are ring members, where 1, 2, 3 or 4 of the ring atoms of hetaryl are selected from nitrogen and oxygen, while the remainder of these atoms are carbon atoms, where mono- or polycyclic aryl are unsubstituted or substituted by 1, 2, 3 or 4 identical or different radicals R";
- R" is selected from fluorine, cyclopropyl, cyclobutyl, phenyl, CN, $OCH_3$, $CH_3$, $N(CH_3)_2$, C(O)$CH_3$, CH=$CH_2$, CH=$CHCH_3$, $CH_2$—CH=$CH_2$, $CH_2$—CH=CH—$CH_3$, $CH_2$—C≡CH and $CH_2$—C≡C—$CH_3$;
- n on each occurrence is 0, 1, 2 or 3.

The above compounds are particularly useful in the preparation of thermoplastic resins, in particular for optical resins as defined herein, in particular for polycarbonate resins polyestercarbonate resins or polyester resins, especially for polycarbonate resins.

When used as monomers for the preparation of optical resins, in particular polycarbonate resins, the compounds of the formula (I) provide for higher refractive indices of the resins than the monomers of the formula (A). Moreover, compounds of formula (I) provide for high transparency of the resins and they do not significantly impair other optical properties and the mechanical properties of the resins. In particular, these resins fulfil the other requirements of optical resins, such as low Abbe's number, a high degree of transparency and low birefringence. Apart from that, the monomers of formula (I) can be easily prepared and obtained in high yields and high purity. In particular, the compounds of formula (I) can be obtained in crystalline form, which allows for an efficient purification to the degree required in the preparation of optical resins. In particular, the compounds of formula (I) can be obtained in a purity which provides for low haze, which is in particular important for the use in the preparation of optical resins. Compounds of formula (I), which do not bear color-imparting radicals, such as some of the radicals Ar, R and R', can also be obtained in a purity, which provides for a low yellowness index Y.I., as determined in accordance with ASTM E313, which may also be important for the use in the preparation of optical resins.

The invention also relates to a thermoplastic resin comprising a polymerized unit of the compounds of formula (I), i.e. a thermoplastic resin comprising a structural unit represented by formula (II) below

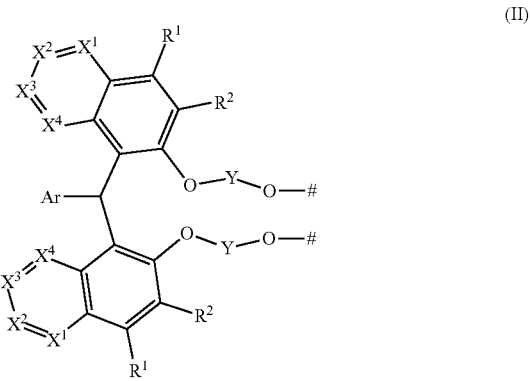

where
- # represents a connection point to a neighboring structural unit;
- and where $R^1$, $R^2$, Ar, $X^1$, $X^2$, $X^3$, $X^4$ and Y are as defined herein.

The invention further relates to a thermoplastic resin selected from copolycarbonate resins, copolyestercarbonate resins and copolyester resins, where the thermoplastic resin in addition to the structural units of formula (II) also comprises other structural units, in particular those of the formula (V),

where
represents a connection point to a neighboring structural unit;
$A^3$ is a polycyclic radical bearing at least 2 benzene rings, wherein the benzene rings may be connected by A' and/or directly fused to each other and/or fused by a non-benzene carbocycle, where $A^3$ is unsubstituted or substituted by 1, 2 or 3 radicals $R^{aa}$, which are selected from the group consisting of halogen, $C_1$-$C_6$-alkyl, $C_5$-$C_6$-cycloalkyl and phenyl;
A' is selected from the group consisting of a single bond, O, C=O, S, $SO_2$, $CH_2$, CH—Ar", $CHAr"_2$, $CH(CH_3)$, $C(CH_3)_2$ and a radical A"

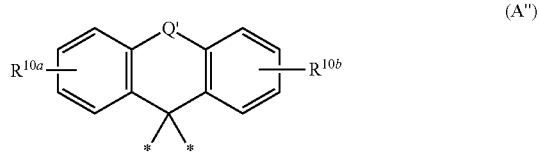

where
Q' represents a single bond, O, NH, C=O, $CH_2$ or CH=CH; and
$R^{10a}$, $R^{10b}$, independently of each other are selected from the group consisting of hydrogen, fluorine, CN, R, OR, $CH_kR_{3-k}$, $NR_2$, C(O)R and $C(O)NH_2$;
Ar" is selected from the group consisting of mono- or polycyclic aryl having from 6 to 26 carbon atoms and mono- or polycyclic hetaryl having a total of 5 to 26 atoms, which are ring members, where 1, 2, 3 or 4 of these atoms are selected from nitrogen, sulphur and oxygen, while the remainder of these atoms are carbon atoms, where Ar" is unsubstituted or substituted by 1, 2 or 3 radicals $R^{ab}$, which are selected from the group consisting of halogen, phenyl and $C_1$-$C_4$-alkyl;
$R^z$ is a single bond, $Alk^1$ or O-$Alk^2$-, where O is bound to $A^3$, and where
$Alk^1$ is $C_2$-$C_4$-alkandiyl; and
$Alk^2$ is $C_2$-$C_4$-alkandiyl.

The invention further relates to an optical device made of a thermoplastic resin as defined above.

The invention further relates to the se of the compound of formula (I) as defined herein as a monomer in the production of the thermoplastic resin as defined herein, in particular as a monomer in the production of a copolycarbonate resin, a copolyestercarbonate resins or a copolyester resin as defined herein.

DETAILED DESCRIPTION OF INVENTION

The compounds of formula (I) may have axial chirality due to the limited rotation along the bonds between the carbon atom to which the moiety Ar is attached and the two bicyclic units and therefore compounds of the formula (I) may exist in the form of a diastereomeric mixture of the three configurational isomers, as a mixture of the two enantiomers, or in the form of one of the pure diastereomers, i.e. one of the two enantiomers or of the meso form. The present invention relates to the diastereomeric mixture, the enantiomeric mixture as well as to the pure diastereomers of the compounds of formula (I).

In terms of the present invention, the term "alkylene group having 1, 2, 3 or 4 carbon atoms" is alternatively also designated "$C_1$-$C_4$-alkandiyl group" and refers to a bivalent, saturated, aliphatic hydrocarbon radical having 1, 2, 3 or 4 carbon atoms. Examples of $C_1$-$C_4$-alkandiyl are in particular linear alkandiyl such as methandiyl (=$CH_2$), 1,2-ethandiyl (=$CH_2CH_2$), 1,3-propandiyl (=$CH_2CH_2CH_2$) and 1,4-butdandiyl (=$CH_2CH_2CH_2CH_2$), but also branched alkandiyl such as 1-methyl-1,2-ethandiyl, 1-methyl-1,2-propandiyl, 2-methyl-1,2-propandiyl, 2-methylpropandiyl and 1,3-butandiyl.

In terms of the present invention, the term "monocyclic aryl" refers to phenyl.

In terms of the present invention, the term "polycyclic aryl" refers to
(i) an aromatic polycyclic hydrocarbon radical, i.e. a completely unsaturated polycyclic hydrocarbon radical, where each of the carbon atoms is part of a conjugate π-electron system,
(ii) a polycyclic hydrocarbon radical which bears 1 phenyl ring which is fused to a saturated or unsaturated 4 to 10-membered mono- or bicyclic hydrocarbon ring,
(iii) a polycyclic hydrocarbon radical which bears at least 2 phenyl rings which are linked to each other by a covalent bond or which are fused to each other directly and/or which are fused to a saturated or unsaturated 4 to 10-membered mono- or bicyclic hydrocarbon ring.

Usually, polycyclic aryl has from 9 to 26, e.g. 9, 10, 12, 13, 14, 16, 17, 18, 19, 20, 22, 24, 25 or 26 carbon atoms, in particular from 10 to 20 carbon atoms, especially 10, 12, 13, 14 or 16 carbon atoms.

In this context, polycyclic aryl bearing 2, 3 or 4 phenyl rings which are linked to each other via a single bond include e.g. biphenylyl and terphenylyl. Polycyclic aryl bearing 2, 3 or 4 phenyl rings which are directly fused to each other include e.g. naphthyl, anthracenyl, phenanthrenyl, pyrenyl and triphenylenyl. Polycyclic aryl bearing 2, 3 or 4 phenyl rings which are fused to a saturated or unsaturated 4- to 10-membered mono- or bicyclic hydrocarbon ring include e.g. 9H-fluorenyl, biphenylenyl, tetraphenylenyl, acenaphthenyl (1,2-dihydroacenaphthylenyl), acenaphthylenyl, 9,10-dihydroanthracen-1-yl, 1,2,3,4-tetrahydrophenanthrenyl, 5,6,7,8-tetrahydrophenanthrenyl, cyclopent[fg]acenaphthylenyl, phenalenyl, fluoranthenyl, benzo[k]fluoranthenyl, perylenyl, 9,10-dihydro-9,10[1',2']-benzenoanthracenyl, dibenzo[a,e][8]annulenyl, 9,9'-spirobi[9H-fluoren]yl and spiro[1H-cyclobuta[de]naphthalene-1,9'-[9H]fluoren]yl.

Polycyclic aryl includes, by way of example naphthyl, 9H-fluorenyl, phenanthryl, anthracenyl, pyrenyl, acenaphthenyl, acenaphthylenyl, 2,3-dihydro-1H-indenyl, 5,6,7,8-tetrahydro-naphthalenyl, cyclopent[fg]acenaphthylenyl, 2,3-dihydrophenalenyl, 9,10-dihydroanthracen-1-yl, 1,2,3,4-tetrahydrophenanthrenyl, 5,6,7,8-tetrahydrophenanthrenyl, fluoranthenyl, benzo[k]fluoranthenyl, biphenylenyl, triphenylenyl, tetraphenylenyl, 1,2-dihydroacenaphthylenyl, dibenzo[a,e][8]annulenyl, perylenyl, biphenylyl, terphenylyl, naphthylenphenyl, phenanthrylphenyl, anthracenylphenyl, pyrenylphenyl, 9H-fluorenylphenyl, di(naphthylen)phenyl, naphthylenbiphenyl, tri(phenyl)phenyl, tetra(phenyl)phenyl, pentaphenyl(phenyl), phenylnaphthyl, binaphthyl, phenanthrylnaphthyl, pyrenylnaphthyl, phenylanthracenyl, biphenylanthracenyl, naphthalenylanthracenyl, phenanthrylanthracenyl, dibenzo[a,e][8]annulenyl, 9,10-dihydro-9,10

[1',2']benzoanthracenyl, 9,9'-spirobi-9H-fluorenyl and spiro [1H-cyclobuta[de]naphthalene-1,9'-[9H]fluoren]yl.

In terms of the present invention, the term "monocyclic hetaryl" refers to a heteroaromatic monocycle, where the ring member atoms are part of a conjugate π-electron system, where the heteroaromatic monocycle has 5 or 6 ring atoms, which comprise 1, 2, 3 or 4 nitrogen atoms or 1 oxygen atom and 0, 1, 2 or 3 nitrogen atoms, or 1 sulphur atom and 0, 1, 2 or 3 nitrogen atoms, where the remainder of the ring atoms are carbon atoms. Examples include furyl (=furanyl), pyrrolyl (=1H-pyrrolyl), thienyl (=thiophenyl), imidazolyl (=1H-imidazolyl), pyrazolyl (=1H-pyrazolyl), 1,2,3-triazolyl, 1,2,4-triazolyl, tetrazolyl, oxazolyl, isoxazolyl, 1,3,4-oxadiazolyl, pyridyl (=pyridinyl), pyrazinyl, pyridazinyl, pyrimidinyl and triazinyl.

In terms of the present invention, the term "polycyclic hetaryl" refers to heteroaromatic polycyclic radicals, which bear a monocyclic hetaryl ring as defined above and at least one, e.g. 1, 2, 3, 4 or 5, further aromatic rings selected from phenyl and heteroaromatic monocycles as defined above, where the aromatic rings of polycyclic hetaryl are linked to each other by a covalent bond and/or fused to each other directly and/or fused to a saturated or unsaturated 4 to 10-membered mono- or bicyclic hydrocarbon ring. The term "polycyclic hetaryl" also refers to heteroaromatic polycyclic radicals, which bear at least one saturated or partially unsaturated 5- or 6-membered heterocyclic ring bearing 1 or 2 heteroatoms selected from oxygen, sulphur and nitrogen as ring atoms, such as 2H-pyran, 4H-pyran, thiopyran, 1,4-dihydropyridin, 4H-1,4-oxazin 4H-1,4-thiazin or 1,4-dioxin and at least one, e.g. 1, 2, 3, 4 or 5, further aromatic rings selected from phenyl and heteroaromatic monocycles, where at least one of the further aromatic rings is directly fused to the saturated or partially unsaturated 5- or 6-membered heterocyclic radical and where the remainder of further aromatic rings of polycyclic hetaryl are linked to each other by a covalent bond or fused to each other directly and/or fused to a saturated or unsaturated 4 to 10-membered mono- or bicyclic hydrocarbon ring. Usually polycyclic hetaryl has 9 to 26 ring atoms in particular 9 to 20 ring atoms, which comprise 1, 2, 3 or 4 atoms selected from nitrogen atoms and oxygen atoms, where the remainder of the ring atoms are carbon atoms.

Examples of polycyclic hetaryl include, but are not limited to, benzofuryl, benzothienyl, dibenzofuranyl (=dibenzo[b,d]furanyl), dibenzothienyl (=dibenzo[b,d]thienyl), naphthofuryl, furo[3,2-b]furanyl, furo[2,3-b]furanyl, furo[3,4-b]furanyl, oxanthrenyl, indolyl (=1H-indolyl), isoindolyl (=2H-isoindolyl), carbazolyl, indolizinyl, benzopyrazolyl, benzimidazolyl, benzoxazolyl, benzo[cd]indolyl, 1H-benzo[g]indolyl, quinolinyl, isoquinolinyl, acridinyl, phenazinyl, quinazolinyl, quinoxalinyl, phenoxazinyl, benzo[b][1,5]naphthyridinyl, cinnolinyl, 1,5-naphthyridinyl, 1,8-naphthyridinyl, phenylpyrrolyl, naphthylpyrrolyl, dipyridyl, phenylpyridyl, naphthylpyridyl, pyrido[4,3-b]indolyl, pyrido[3,2-b]indolyl, pyrido[3,2-g]quinolinyl, pyrido[2,3-b][1,8]naphthyridinyl, pyrrolo[3,2-b]pyridinyl, pteridinyl, puryl, 9H-xanthenyl, 2H-chromenyl, phenanthridinyl, phenanthrolinyl, furo[3,2-f][1]benzofuranyl, furo[2,3-f][1]benzofuranyl, furo[3,2-g]quinolinyl, furo[2,3-g]quinolinyl, furo[2,3-g]quinoxalinyl, benzo[g]chromenyl, pyrrolo[3,2,1-hi]indolyl, benzo[g]quinoxalinyl, benzo[f]quinoxalinyl, and benzo[h]isoquinolinyl.

In terms of the present invention, the term "optical device" refers to a device that is transparent for visible light and manipulates light beams, in particular by refraction. Optical devices include but are not limited to prisms, lenses, optical films and combinations thereof, especially lenses, e.g. lenses for cameras and lenses for glasses, and optical films.

The remarks made below as to preferred embodiments of the variables (substituents) of the compounds of formula (I) and of the structural units of formula (II) are valid on their own as well as preferably in combination with each other, as well as in combination with the stereoisomers thereof.

The remarks made below concerning preferred embodiments of the variables further are valid on their own as well as preferably in combination with each other concerning the compounds of formula (I) and the structural units of formula (II), where applicable, as well as concerning the uses and methods according to the invention and the composition according to the invention.

In formula (I) and likewise in formula (II), the variables Y, $R^1$, $R^2$, Ar, $X^1$, $X^2$, $X^3$ and $X^4$ on their own or preferably in any combination preferably have the following meanings:

The variables Y in formulae (I) and (II) are in particular linear alkylene groups having 2, 3 or 4 carbon atoms, such as e.g. 1,2-ethandiyl ($CH_2$—$CH_2$), 1,3-propandiyl or 1,4-butandiyl. Especially, the variables Y are 1,2-ethandiyl.

According to a first group (1) of embodiments, the radicals $R^1$ and $R^2$ are selected independently of one another from hydrogen and a radical $R^a$. Preferably, both radicals $R^1$ and $R^2$ are hydrogen. However, it may also be preferred that either $R^1$ or $R^2$ is a radical $R^a$. In this context, the radical $R^a$ is preferably selected from the group consisting of fluorine, cyclopropyl, cyclobutyl, CN, $OCH_3$, $CH_3$, $N(CH_3)_2$, $C(O)CH_3$, CH=$CH_2$, CH=$CHCH_3$, $CH_2$—CH=$CH_2$, $CH_2$—CH=CH—$CH_3$, $CH_2$—C≡CH and $CH_2$—C≡C—$CH_3$. In particular, $R^a$, if present, is selected from the group consisting of fluorine, CN, $OCH_3$, $CH_3$ and CH=$CH_2$, especially from the group consisting of fluorine, CH=$CH_2$ and CN, and particularly from CH=$CH_2$ and CN.

According to a second group (2) of embodiments, $R^1$ and $R^2$ together with the carbon atoms to which they are bound form a fused benzene ring, which is unsubstituted or substituted by one radical $R^a$, where $R^a$ has one of the meanings defined herein, in particular one of the preferred meanings. In this second group of embodiments it is preferred that $R^1$ and $R^2$ together with the carbon atoms to which they are bound form a fused benzene ring, which is unsubstituted. Especially, the radicals $R^1$ and $R^2$ are both hydrogen.

It is preferred that the basic structure of the radical Ar, i.e. the mono/polycyclic aryl or mono/polycyclic hetaryl group, is unsubstituted or bears 1, 2 or 3, in particular 1 or 2 and especially 1 radical $R^{Ar}$. Each radical $R^{Ar}$ is typically bound to a carbon atom in any position of the basic structure of the radical Ar. For example, if the basic structure of Ar is phenyl or 1-naphthyl the radicals $R^{Ar}$ may be attached in position 2, 3 or 4 and in position 2, 3, 4, 5, 6, 7 or 8, respectively.

In a particular group (3) of embodiments of the present invention the radical Ar is selected from the group consisting of mono- and polycyclic aryl having a total of 6 to 26 atoms, in particular a total of 6 to 20 carbon atoms, where mono- and polycyclic aryl are unsubstituted or carry 1, 2, 3 or 4 radicals $R^{Ar}$, with $R^{Ar}$ having one of the meanings defined herein, in particular one of the preferred meanings.

In the group (3) of embodiments, the mono- or polycyclic aryl moieties suitable as radical Ar are in particular selected from the group consisting of:
phenyl, naphthyl, phenanthryl, biphenylyl, 2,3-dihydro-1H-indenyl, 1H-indenyl, 5,6,7,8-tetrahydronaphthalenyl, 1,2-dihydroacenaphthylenyl, acenaphthylenyl, 9,10-dihydroanthracen-1-yl, 1,2,3,4-tetrahydrophenanthrenyl, 5,6,7,8-tetrahydrophenanthrenyl, fluorenyl, anthracenyl, pyrenyl, biphenylenyl, triphenylenyl, tetraphenylenyl, 5H-dibenzo[a,d][7]annulenyl, perylenyl, 9,9'-spirobi[9H-fluoren]yl and 10,11-dihydro-5H-dibenzo[a,d][7]annulenyl, dibenzo[a,e][8]annulenyl, where mono- or polycyclic aryl is unsubstituted or substituted by 1 radical $R^{Ar}$.

In the group (3) of embodiments, the radical Ar in formulae (I) and (II) is more preferably a mono- or polycyclic aryl selected from the group consisting of phenyl, naphthyl, specifically 1- or 2-naphthyl, phenanthryl, specifically 9-phenanthryl, 1,2-dihydroacenaphthylenyl, specifically 1,2-dihydroacenaphthylen-5-yl, anthracenyl, specifically 9-anthracenyl, 9H-fluorenyl, specifically 9H-fluoren-2-yl, pyrenyl specifically 3-pyrenyl, and biphenylyl, specifically 3- or 4-biphenylyl, which may be unsubstituted or substituted by 1 radical $R^{Ar}$, with $R^{Ar}$ having one of the meanings defined herein, in particular one of the preferred meanings.

In the group (3) of embodiments, the radical Ar in formulae (I) and (II) is especially a mono- or polycyclic aryl selected from the group consisting of phenyl, naphthyl, specifically 1- or 2-naphthyl, phenanthryl, specifically 9-phenanthryl, 1,2-dihydroacenaphthylenyl, specifically 1,2-dihydroacenaphthylen-5-yl, 9H-fluorenyl, specifically 9H-fluoren-2-yl, biphenylenyl and biphenylyl, specifically 3- or 4-biphenylyl, which may be unsubstituted or substituted by 1 radical $R^{Ar}$, with $R^{Ar}$ having one of the meanings defined herein, in particular one of the preferred meanings.

In the group (3) of embodiments, the radical Ar in formulae (I) and (II) is in particular a mono- or polycyclic aryl selected from the group consisting of phenyl, naphthyl, specifically 1- or 2-naphthyl, phenanthryl, specifically 9-phenanthryl, 1,2-dihydroacenaphthylenyl, specifically 1,2-dihydroacenaphthylen-5-yl, biphenylenyl and biphenylyl, specifically 3- or 4-biphenylyl, which may be unsubstituted or substituted by 1 radical $R^{Ar}$, with $R^{Ar}$ having one of the meanings defined herein, in particular one of the preferred meanings.

In another particular group (4) of embodiments of the present invention the radical Ar in formulae (I) and (II) is selected from the group consisting of mono- or polycyclic hetaryl having a total of 5 to 26 atoms, which are ring members, where 1, 2, 3 or 4 of these atoms are selected from nitrogen, sulphur and oxygen, while the remainder of these atoms are carbon atoms, where mono- or polycyclic hetaryl are unsubstituted or carry 1, 2, 3 or 4 radicals $R^{Ar}$, with $R^{Ar}$ having one of the meanings defined herein, in particular one of the preferred meanings.

Examples of such radicals include but are not limited to:

furyl, thienyl, pyrrolyl, imidazolyl, pyrazolyl, 1,2,3-triazolyl, 1,2,4-triazolyl, tetrazolyl, oxazolyl, isoxazolyl, thiazolyl, isothiazolyl, 1,3,4-oxadiazolyl, 1,2,4-oxadiazolyl, pyridyl, pyrazinyl, pyridazinyl, pyrimidinyl, triazinyl, benzofuryl, dibenzofuranyl, benzothienyl, dibenzothienyl, naphthofuryl, furo[3,2-b]furanyl, furo[2,3-b]furanyl, furo[3,4-b]furanyl, oxanthrenyl, indolyl, isoindolyl, carbazolyl, indolizinyl, benzopyrazolyl, benzimidazolyl, benzoxazolyl, benzo[cd]indolyl, 1H-benzo[g]indolyl, 3H-benzo[e]indolyl, 1H-benzo[f]indolyl, quinolinyl, isoquinolinyl, acridinyl, phenazinyl, quinazolinyl, quinoxalinyl, phenoxazinyl, benzo[b][1,5]naphthyridinyl, benzo[b][1,8]naphthyridin-3-yl, cinnolinyl, 1,5-naphthyridinyl, 1,8-naphthyridinyl, phenylpyrrolyl, naphthylpyrrolyl, dipyridyl, phenylpyridyl, naphthylpyridyl, pyrido[4,3-b]indolyl, pyrido[3,2-b]indolyl, pyrido[2,3-g]quinolinyl, pyrido[3,2-g]quinolinyl, pyrido[2,3-b][1,8]naphthyridinyl, pyrrolo[3,2-b]pyridinyl, pteridinyl, puryl, 9H-xanthenyl, 2H-chromenyl, 4H-chromenyl, phenanthridinyl, phenanthrolinyl, furo[3,2-f][1]benzofuranyl, furo[2,3-f][1]benzofuranyl, furo[3,2-g]quinolinyl, furo[2,3-g]quinolinyl, furo[2,3-g]quinoxalinyl, 2H-benzo[g]chromenyl, 4H-benzo[g]chromenyl, 3H-benzo[f]chromenyl, 1-benzo[f]chromenyl, pyrrolo[3,2,1-hi]indolyl, benzo[g]quinoxalinyl, benzo[f]quinoxalinyl, and benzo[h]isoquinolinyl.

In the group (4) of embodiments, the radical Ar in formulae (I) and (II) is preferably a mono- or polycyclic hetaryl selected from the group consisting of furyl, benzofuryl, benzothienyl, naphthofuryl, dibenzofuranyl, dibenzothienyl, 9H-xanthenyl, 2H-chromenyl, 4H-chromenyl, 2H-benzo[g]chromenyl, 4H-benzo[g]chromenyl, 3H-benzo[f]chromenyl, 1H-benzo[f]chromenyl, furo[3,2-b]furanyl, furo[2,3-b]furanyl, furo[3,4-b]furanyl, 2,3-dihydro-1,4-benzodioxinyl, oxanthrenyl, furo[3,2-f][1]benzofuranyl, furo[2,3-f][1]benzofuranyl, pyrrolyl, indolyl, isoindolyl, carbazolyl, indolizinyl, benzo[cd]indolyl, 1H-benzo[g]indolyl, 3H-benzo[e]indolyl, 1H-benzo[f]indolyl, pyridyl, quinolinyl, isoquinolinyl, acridinyl, phenanthridinyl, benzo[f]isoquinolinyl, benzo[h]isoquinolinyl, imidazolyl, pyrazolyl, pyrazinyl, pyridazinyl, pyrimidinyl, benzopyrazolyl, benzimidazolyl, quinazolinyl, quinoxalinyl, cinnolinyl, 1,5-naphthyridinyl, 1,8-naphthyridinyl, dipyridyl, pyrido[4,3-b]indolyl, pyrido[3,2-b]indolyl, pyrrolo[3,2-b]pyridinyl, phenazinyl, benzo[b][1,5]naphthyridinyl, phenanthrolinyl, benzo[b][1,8]naphthyridin-3-yl, pyrido[2,3-g]quinolinyl, pyrido[3,2-g]quinolinyl, benzo[g]quinoxalinyl, benzo[f]quinoxalinyl, 1,2,3-triazolyl, 1,2,4-triazolyl, triazinyl, pyrido[2,3-b][1,8]naphthyridinyl, tetrazolyl, oxazolyl, isoxazolyl, 1,3,4-oxadiazolyl, 1,2,4-oxadiazolyl, benzoxazolyl, phenoxazinyl, furo[3,2-g]quinolinyl, furo[2,3-g]quinolinyl and furo[2,3-g]quinoxalinyl, where mono- or polycyclic hetaryl is unsubstituted or substituted by 1 radical $R^{Ar}$, with $R^{Ar}$ having one of the meanings defined herein, in particular one of the preferred meanings.

In the group (4) of embodiments, the radical Ar in formulae (I) and (II) is in particular a mono- or polycyclic hetaryl selected from the group consisting of dibenzo[b,d]furanyl, specifically 2-, 3 or 4-dibenzo[b,d]furanyl, dibenzo[b,d]thienyl, specifically 2-, 3- or 4-dibenzo[b,d]thienyl, pyrrolyl, specifically 2- or 3-pyrrolyl, indolyl, specifically 3-indolyl, pyridyl, specifically 2-, 3- or 4-pyridyl, quinolinyl, specifically 2-, 3- or 4-quinolinyl, isoquinolinyl, specifically 1- or 4-isoquinolinyl, and pyrimidinyl, specifically 5-pyrimidinyl, which may be unsubstituted or substituted by 1 radical $R^{Ar}$, with $R^{Ar}$ having one of the meanings defined herein, in particular one of the preferred meanings.

In the context of the radical Ar, the radicals $R^{Ar}$, if present, are preferably independently selected from the group consisting of fluorine, cyclopropyl, cyclobutyl, CN, R, OR, $CH_nR_{3-n}$, $NR_2$, C(O)R, C(O)NH$_2$, CH=CH$_2$, CH=CHR', CH$_2$—CH=CH$_2$, CH$_2$—CH=CHR', CH$_2$—C≡CH and CH$_2$—C≡CR', where the variables R and R' have the meanings defined herein, in particular the preferred meanings.

Preferably, the radicals $R^{Ar}$, if present, are independently selected from the group consisting of fluorine, cyclopropyl, cyclobutyl, CN, CH$_3$, OCH$_3$, phenyl, naphthyl, anthracenyl, phenanthryl, 9H-fluorenyl, biphenylyl, dibenzo[b,d]furanyl, pyrrolyl, indolyl, pyridyl, quinolinyl, isoquinolinyl, pyrimidinyl, phenoxy, naphthyloxy, N(CH$_3$)$_2$, C(O)CH$_3$, CH=CH$_2$, CH=CHCH$_3$, CH$_2$—CH=CH$_2$, CH$_2$—CH=CH—CH$_3$, CH$_2$—C≡CH, CH$_2$—C≡C—CH$_3$. In this context, R' is preferably selected from the group consisting of methyl, phenyl, naphthyl, phenanthryl, biphenylyl, dibenzo[b,d]furanyl, pyrrolyl, indolyl, pyridyl, quinolinyl, isoquinolinyl and pyrimidinyl.

More preferably, the radicals $R^{Ar}$, if present, are selected from the group consisting of fluorine, cyclopropyl, cyclobutyl, CN, $CH_3$, $OCH_3$, phenyl, phenoxy, naphthyloxy, $N(CH_3)_2$, $C(O)CH_3$, $CH=CH_2$, $CH=CHCH_3$, $CH_2—CH=CH_2$, $CH_2—CH=CH—CH_3$, $CH_2—C\equiv CH$ and $CH_2—C\equiv C—CH_3$, especially from CN, $CH_3$, $OCH_3$, $CH=CH_2$ and phenyl, and in particular from CN, $CH=CH_2$ and phenyl.

In particular, the radicals $R^{Ar}$, if present, are selected from the group consisting of CN, $CH_3$, $OCH_3$, phenyl and phenoxy, especially from the group consisting of CN and phenoxy.

In particular the radical Ar is selected from the group consisting of radicals of the formulae Ar-1 to Ar-18;

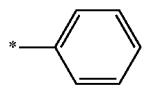

Ar-1

Ar-2

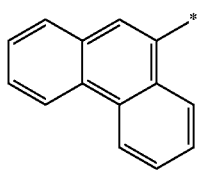

Ar-3

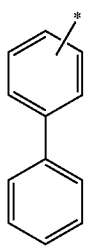

Ar-4

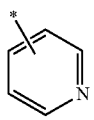

Ar-5

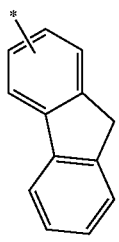

Ar-6

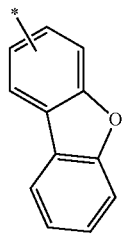

Ar-7

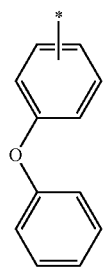

Ar-8

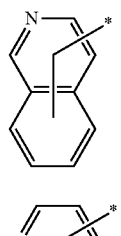

Ar-9

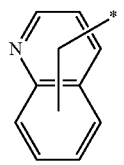

Ar-10

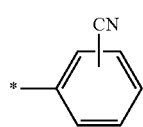

Ar-11

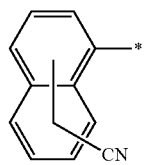

Ar-12

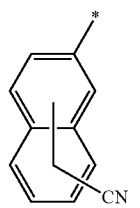

Ar-13

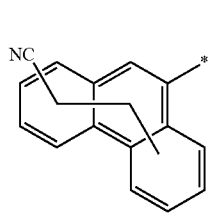

Ar-14

-continued

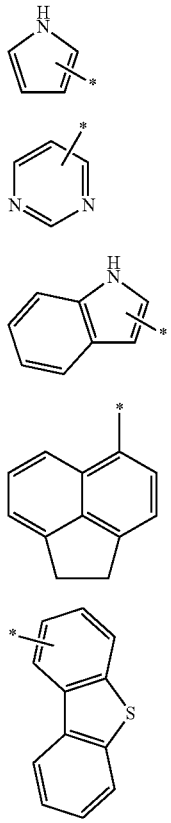

Ar-15

Ar-16

Ar-17

Ar-18

Ar-19 where * indicates the point of attachment to the remainder of the molecule of the formula (I).

Particular examples of radicals Ar of the formulae Ar-1 to Ar-19 are phenyl, 1-naphthyl, 2-naphthyl, 9-phenanthryl, 4-phenylphenyl (=4-biphenylyl), 3-phenylphenyl (=3-biphenylyl), 4-phenoxyphenyl, 9H-fluoren-2-yl, 1,2-dihydroacenaphthylen-5-yl, dibenzofuran-2-yl, dibenzofuran-3-yl, dibenzofuran-1-yl, dibenzofuran-4-yl, dibenzothien-2-yl, dibenzothien-3-yl, dibenzothien-1-yl, dibenzothien-4-yl, 4-quinolinyl, 2-quinolinyl, 3-quinolinyl, 5-quinolinyl, 6-quinolinyl, 7-quinolinyl, 8-quinolinyl, 1-isoquinolinyl, 4-isoquinolinyl, 3-isoquinolinyl, 5-isoquinolinyl, 6-isoquinolinyl, 7-isoquinolinyl, 8-isoquinolinyl, 1H-indol-3-yl, 1H-pyrrol-2-yl, 1H-pyrrol-3-yl, 2-pyridyl, 3-pyridyl, 4-pyridyl, 5-pyrimidinyl, 2-cyanophenyl, 3-cyanophenyl, 4-cyanophenyl, 4-cyano-1-naphthyl, 5-cyano-1-naphthyl, 3-cyano-1-naphthyl, 6-cyano-1-naphthyl, 4-cyano-2-naphthyl, 6-cyano-2-naphthyl, 5-cyano-2-naphthyl, 7-cyano-2-naphthyl, 8-cyano-2-naphthyl, 2-cyano-9-phenanthryl, 3-cyano-9-phenanthryl, 4-cyano-9-phenanthryl, 5-cyano-9-phenanthryl, 6-cyano-9-phenanthryl and 7-cyano-9-phenanthryl.

Particularly preferred radicals Ar of the formulae Ar-1 to Ar-19 are selected from the group consisting of phenyl, 1-naphthyl, 2-naphthyl, 9-phenanthryl, 4-phenylphenyl (=4-biphenylyl), 3-phenylphenyl (=3-biphenylyl), 4-phenoxyphenyl, 9H-fluoren-2-yl, 1,2-dihydroacenaphthylen-5-yl, dibenzofuran-2-yl, dibenzofuran-3-yl, dibenzofuran-4-yl, dibenzo[b,d]thien-2-yl, dibenzo[b,d]thien-3-yl, dibenzo[b,d]thien-4-yl, 4-quinolinyl, 2-quinolinyl, 3-quinolinyl, 1-isoquinolinyl, 4-isoquinolinyl, 1H-indol-3-yl, 1H-pyrrol-2-yl, 1H-pyrrol-3-yl, 2-pyridyl, 3-pyridyl, 4-pyridyl, 5-pyrimidinyl, 2-cyanophenyl, 3-cyanophenyl, 4-cyanophenyl, 4-cyano-1-naphthyl, 5-cyano-1-naphthyl, 4-cyano-2-naphthyl and 6-cyano-2-naphthyl.

Preference is given to those compounds of formula (I) and likewise to those units of formula (II), where either all of the variables $X^1$, $X^2$, $X^3$, $X^4$ are CH or C—$R^x$ or where in each ring at most one of $X^1$, $X^2$, $X^3$ and $X^4$ is N, while the others are selected from CH and C—$R^x$.

In a particular group (5) of embodiments of the present invention the variables $X^1$, $X^2$, $X^3$ and $X^4$ are CH or C—$R^x$, where the radical $R^x$ has one of the meanings defined herein, in particular one of the preferred meanings. Preferably, either all variables $X^1$, $X^2$, $X^3$ or $X^4$ are CH or one of the variables $X^1$, $X^2$, $X^3$ and $X^4$ is C—$R^x$ and the three remaining variables are CH. In particular, the variables $X^1$ and $X^4$ are both CH, while one of $X^2$ and $X^3$ is CH while the other is CH or C—$R^x$.

In another particular group (6) of embodiments of the present invention one of the four variables $X^1$, $X^2$, $X^3$ or $X^4$ is N and the three remaining variables are CH or C—$R^x$ and in particular are all three CH, where the radical $R^x$ has one of the meanings defined herein, in particular one of the preferred meanings.

A skilled person will readily appreciate that the meanings of $R^1$ and $R^2$ of group (1) of embodiments may be combined with the meanings of Ar of one of group (3) or group (4) of embodiments and also with the meanings of $X^1$, $X^2$, $X^3$ or $X^4$ of one of group (5) or group (6) of embodiments. A skilled person will also appreciate that the meanings of $R^1$ and $R^2$ of group (2) of embodiments may be combined with the meanings of Ar of one of group (3) or group (4) of embodiments and also with the meanings of $X^1$, $X^2$, $X^3$ or $X^4$ of one of group (5) or group (6) of embodiments.

Apart from that and if not stated otherwise, the radicals, $R^a$, $R^x$, R, R' and R" either alone or preferably in combination have the following meanings.

$R^a$ is in particular selected from the group consisting of fluorine, cyclopropyl, cyclobutyl, CN, $CH_3$, $OCH_3$, phenyl, naphthyl, anthracenyl, phenanthryl, biphenylyl, dibenzo[b,d]furanyl, pyrrolyl, indolyl, pyridyl, quinolinyl, isoquinolinyl, pyrimidinyl, phenoxy, naphthyloxy, $N(CH_3)_2$, $C(O)CH_3$, $CH=CH_2$, $CH=CHCH_3$, $CH_2$—$CH=CH_2$, $CH_2$—$CH=CH$—$CH_3$, $CH_2$—$C≡CH$ and $CH_2$—$C≡C$—$CH_3$. More preferably, the radical $R^a$ is selected from the group consisting of fluorine, cyclopropyl, cyclobutyl, CN, $CH_3$, $OCH_3$, phenyl, naphthyl, anthracenyl, phenanthrenyl, pyridyl, phenoxy, naphthyloxy, $N(CH_3)_2$, $C(O)CH_3$, $CH=CH_2$, $CH=CHCH_3$, $CH_2$—$CH=CH_2$, $CH_2$—$CH=CH$—$CH_3$, $CH_2$—$C≡CH$ and $CH_2$—$C≡C$—$CH_3$. In particular, the radical $R^a$ is selected from the group consisting of fluorine, cyclopropyl, CN, $OCH_3$, $CH=CH_2$, phenyl and phenoxy, more particular from CN, $CH=CH_2$ and phenyl, and especially is CN.

Preferably, the radical $R^x$ is selected from the group consisting of bromine, fluorine, cyclopropyl, cyclobutyl, CN, $CH_3$, $OCH_3$, phenyl, naphthyl, anthracenyl, phenanthryl, biphenylyl, dibenzo[b,d]furanyl, pyrrolyl, indolyl, pyridyl, quinolinyl, isoquinolinyl, pyrimidinyl, phenoxy, naphthyloxy, $N(CH_3)_2$, $C(O)CH_3$, $CH=CH_2$, $CH=CHCH_3$, $CH_2$—$CH=CH_2$, $CH_2$—$CH=CH$—$CH_3$, $CH_2$—$C≡CH$ and $CH_2$—$C≡C$—$CH_3$. More preferably, the radical $R^x$ is selected from the group consisting of bromine, CN, $CH_3$, $OCH_3$, phenyl, naphthyl, anthracenyl, phenanthryl, pyridyl, phenoxy, naphthyloxy, $N(CH_3)_2$, $C(O)CH_3$, $CH=CH_2$, $CH_2$—$C≡CH$ and $CH_2$—$C≡C$—$CH_3$. In particular, the radical $R^x$ is selected from the group consisting of bromine, CN, $OCH_3$, $CH=CH_2$, phenyl, naphthyl, phenanthryl and phenoxy, more particular from bromine, CN, CH=CH$_2$ and phenyl, and especially from bromine, CN and phenyl.

Preferably, the mono- or polycyclic aryl moieties suitable as radicals R and R' are selected from the group consisting of phenyl, naphthyl, phenanthryl, biphenylyl, dibenzo[b,d]furanyl, pyrrolyl, indolyl, pyridyl, quinolinyl, isoquinolinyl and pyrimidinyl. In particular, the radicals R or R' are selected from the group consisting of phenyl, naphthyl, specifically 1- or 2-naphthyl and phenanthryl, specifically 9-phenanthryl.

Preferably, the one or more radicals R" are independently selected from fluorine, phenyl, CN, OCH$_3$, CH$_3$, CH=CH$_2$ and CH=CHCH$_3$, in particular from fluorine, phenyl and CN.

In a particular group (7) of preferred embodiments of the present invention the compound of the formula (I) and likewise the structural unit of formula (II) bear at least one radical $R^{Ar}$, $R^x$, $R^1$ or $R^2$ which is selected from CN, CH=CH$_2$, phenyl or phenoxy, and in particular is CN.

A skilled person will readily appreciate that the particular group (7) of embodiments may be combined with the meanings of $R^1$ and $R^2$ of one of group (1) or group (2) of embodiments, with the meanings of Ar of one of group (3) or group (4) of embodiments and also with the meanings of $X^1$, $X^2$, $X^3$ or $X^4$ of one of group (5) or group (6) of embodiments.

In the group (7) of embodiments of the present invention a particular subgroup (7a) of embodiments relates to the compounds of the formula (I) and the structural units of formula (II), which bear at least one radical $R^{Ar}$ or $R^x$ which is CN or CH=CH$_2$, and especially is CN.

In yet a further group (8) of embodiments of the present invention the compound of the formula (I) and likewise the structural unit of formula (II) do not bear any radical $R^{Ar}$ or $R^x$.

A skilled person will readily appreciate that the particular group (8) of embodiments may be combined with the meanings of $R^1$ and $R^2$ of one of group (1) or group (2) of embodiments, with the meanings of Ar of one of group (3) or group (4) of embodiments and also with the meanings of $X^1$, $X^2$, $X^3$ or $X^4$ of one of group (5) or group (6) of embodiments.

In a particular subgroup (1a) of groups (1) and (5) of embodiments the compound of the formula (I) is a compound of the formula (Ia):

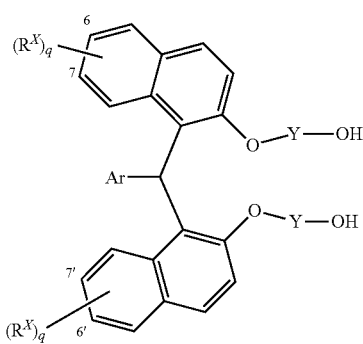

(Ia)

where the radical Ar has one of the meanings defined herein, in particular one of the preferred meanings, the variable q is 0 or 1 and, if q is 1, the radicals $R^x$ are located in in 6,6' or 7,7' positions of the naphthyl ring, with $R^x$ having one of the meanings defined herein, in particular one of the preferred meanings.

In this subgroup (1a) of groups (1) and (5) of embodiments the structural unit of the formula (II) is a structural unit of the formula (IIa):

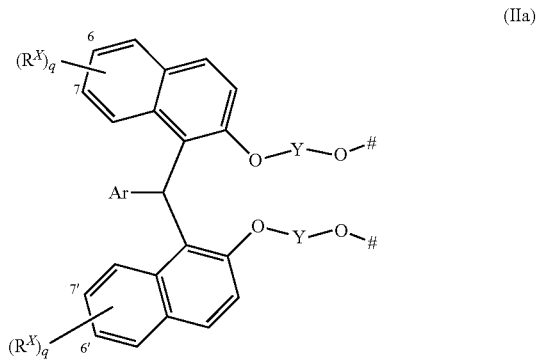

(IIa)

where # represents a connection point to a neighboring structural unit and where the radical Ar has one of the meanings defined herein, in particular one of the preferred meanings, the variable q is 0 or 1 and, if q is 1, the radicals $R^x$ are located in in 6,6' or 7,7' positions of the naphthyl ring, with $R^x$ having one of the meanings defined herein, in particular one of the preferred meanings.

In a particular subgroup (1a.1) of group (1a) of embodiments the variable q in formulae (Ia) and (IIa) is 0.

In another particular subgroup (1a.2) of embodiments the variable q in formulae (Ia) and (IIa), respectively, is 1. In this subgroup (1a.2), the radical $R^x$ is preferably selected from the group consisting of bromine, CN, phenyl, naphthyl, phenanthryl, biphenylyl, dibenzo[b,d]furanyl, pyrrolyl, indolyl, pyridyl, quinolinyl, isoquinolinyl and pyrimidinyl. In this particular subgroup (1a.2) of embodiments the radical $R^x$ is in particular selected from bromine, CN, phenyl, naphthyl and pyridyl. In this particular subgroup (1a.2) of embodiments the radical $R^x$ is particularly selected from bromine, CN, phenyl and naphthyl, and more particularly from bromine, CN and phenyl.

In a particular subgroup (2a) of groups (2) and (5) of embodiments of the invention the compound of the formula (I) is a compound of the formula (Ib):

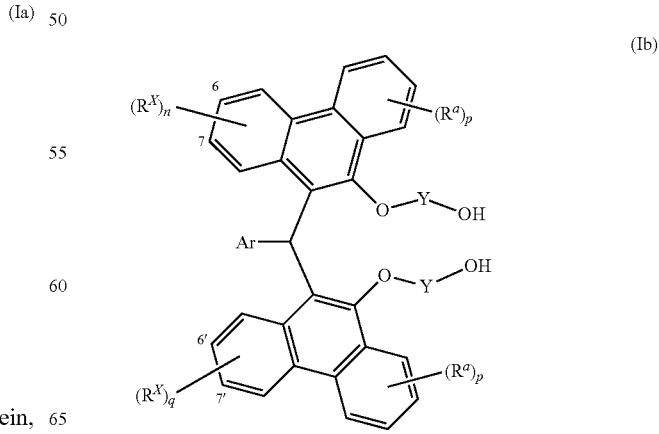

(Ib)

where the radical Ar has one of the meanings defined herein, in particular one of the preferred meanings, the variable q is 0 or 1, the variable p is 0 or 1 and, if q is 1, the radicals $R^x$ are located in in 6,6' or 7,7' positions of the phenanthryl ring, with $R^x$ and $R^a$ having the meanings defined herein, in particular the preferred ones.

In this subgroup (2a) of groups (2) and (5) of embodiments the structural unit of the formula (II) is a structural unit of the formula (IIb):

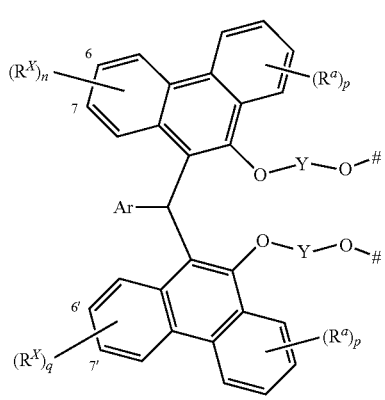

(IIb)

where # represents a connection point to a neighboring structural unit and where the radical Ar has one of the meanings defined herein, in particular one of the preferred meanings, the variable q is 0 or 1, the variable p is 0 or 1 and, if q is 1, the radicals $R^x$ are located in in 6,6' or 7,7' positions of the phenanthryl ring, with $R^x$ and $R^a$ having the meanings defined herein, in particular the preferred ones.

In a particular subgroup (2a.1) of subgroup (2a) of embodiments the variables q and p in formulae (Ib) and (IIb), respectively, are both 0.

In another particular subgroup (2a.2) of subgroup (2a) of embodiments the variable q in formulae (Ib) and (IIb), respectively, is 1 and the variable p in formulae (Ib) and (IIb), is 0.

In a further particular subgroup (2a.3) of subgroup (2a) of embodiments the variable q in formulae (Ib) and (IIb), respectively, is 0 and the p in formulae (Ib) and (IIb), respectively, is 1.

In yet a further particular subgroup (2a.4) of subgroup (2a) of embodiments the variables q and p in formulae (Ib) and (IIb), respectively, are both 1.

In case the variable q in formulae (Ib) and (IIb), respectively, is 1, the radical $R^x$ is preferably selected from the group consisting of bromine, CN, phenyl, naphthyl, phenanthryl, biphenylyl, dibenzo[b,d]furanyl, dibenzo[b,d]thienyl, pyrrolyl, indolyl, pyridyl, quinolinyl, isoquinolinyl and pyrimidinyl. In this context the radical $R^x$ is preferably selected from the group consisting of bromine, CN, phenyl, naphthyl and pyridyl. In this context the radical $R^x$ is in particular selected from the group consisting of bromine, CN, phenyl, and naphthyl, and more particularly from bromine, CN and phenyl.

In case the variable p in formulae (Ib) and (IIb), respectively, is 1, the radical $R^a$ is preferably selected from the group consisting of fluorine, CN, $CH_3$, $OCH_3$, phenyl, naphthyl, anthracenyl, phenanthryl, biphenylyl, dibenzo[b,d]furanyl, dibenzo[b,d]thienyl, pyrrolyl, indolyl, pyridyl, quinolinyl, isoquinolinyl, pyrimidinyl, phenoxy, naphthyloxy, $N(CH_3)_2$, $C(O)CH_3$, $CH=CH_2$, $CH_2-C\equiv CH$ and $CH_2-C\equiv C-CH_3$. In this context the radical $R^a$ is more preferably selected from fluorine, CN, $CH_3$, $OCH_3$, phenyl, naphthyl and pyridyl. In this context the radical $R^a$ is in particular selected from CN, phenyl and naphthyl, and more particularly from CN and phenyl.

In another particular subgroup (1 b) of groups (1) and (6) of embodiments the compound of the formula (I) is a compound of one of formulae (Ic), (Id), (Ie) or (If):

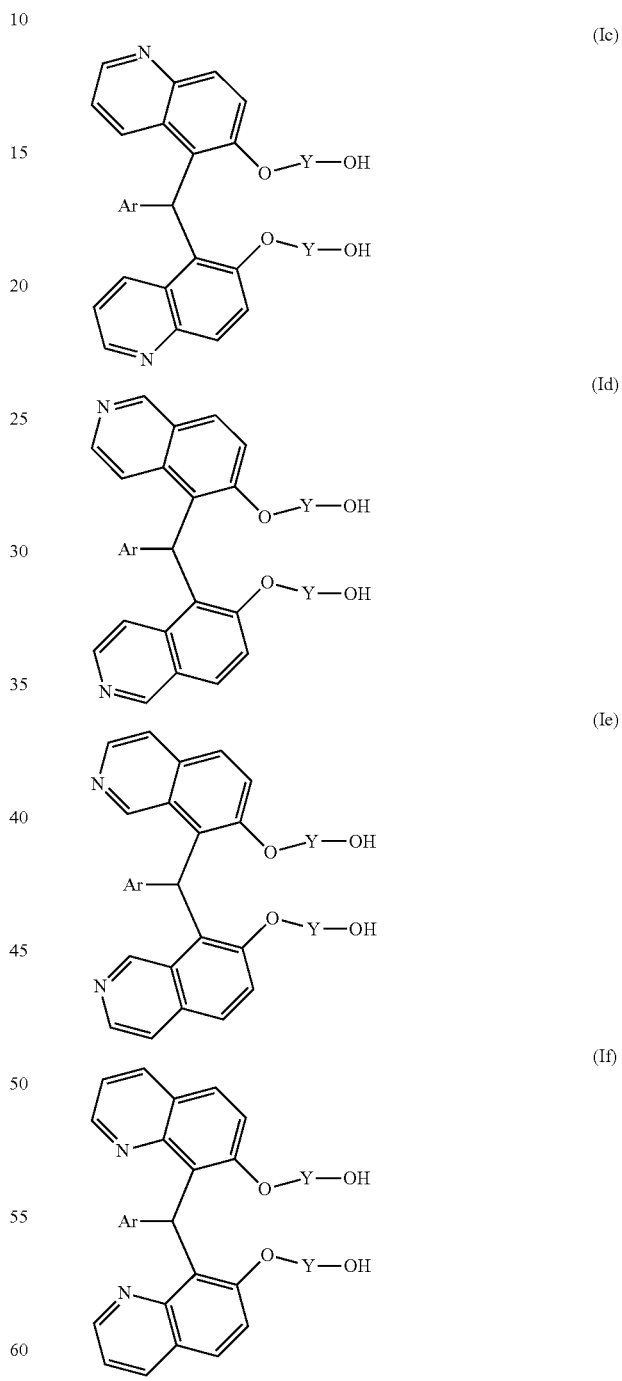

where the radical Ar has one of the meanings defined herein, in particular one of the preferred meanings, and the variables Y are as defined herein and preferably are linear alkylene groups having 2, 3 or 4 carbon atoms, in particular 1,2-ethandiyl.

In this subgroup (1b) of groups (1) and (6) of embodiments the structural unit of the formula (II) is a structural unit of the formulae (IIc), (IId), (IIe) or (IIf):

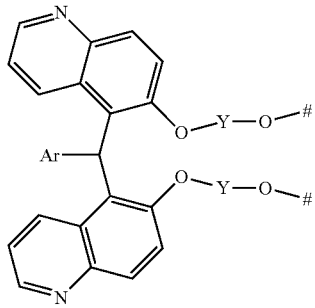
(IIc)

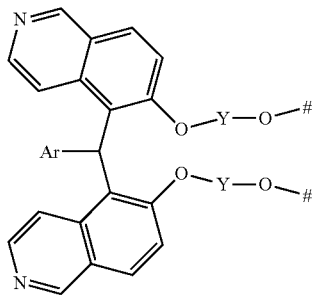
(IId)

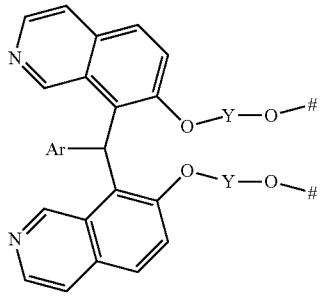
(IIe)

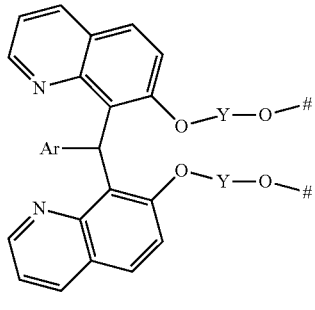
(IIf)

where # represents a connection point to a neighboring structural unit and where the radical Ar has one of the meanings defined herein, in particular one of the preferred meanings, and the variables Y are as defined herein and preferably are linear alkylene groups having 2, 3 or 4 carbon atoms, in particular 1,2-ethandiyl.

In a particular subgroup (1c) of groups (1) and (5) of embodiments the compound of formula (I) is a compound of formula (Ia'), where $R^{x1}$ and $R^{x2}$ are hydrogen or have one of the meanings, in particular the preferred meanings given for $R^x$ as defined herein and Ar is as defined herein and has in particular one of the preferred meanings.

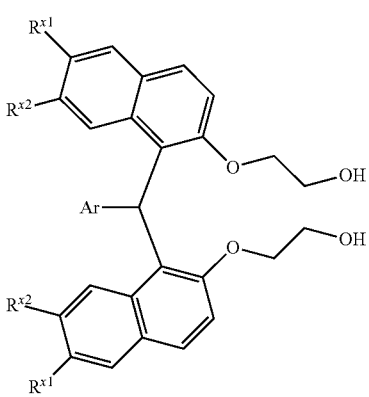
(Ia')

Examples of the compounds of the particular subgroup (1c) are the compounds of formula (Ia'), where the combination of Ar, $R^{x1}$ and $R^{x2}$ as defined in one row of table A below. In the following table A, also the refractive indices no of several compounds of the formula (Ia') at wavelength of 589 nm are summarized. The refractive indices of the compounds of formula (Ia') were calculated by using the computer software ACD/ChemSketch 2012 (Advanced Chemistry Development, Inc.).

TABLE A

| # | $R^{x1}$ | $R^{x2}$ | Ar | $n_D$ (calc.) |
|---|---|---|---|---|
| 1 | H | H | phenyl | 1.67 |
| 2 | H | H | 1-naphthyl | 1.70 |
| 3 | H | H | 2-naphthyl | 1.70 |
| 4 | H | H | 9-phenanthryl | 1.73 |
| 5 | H | H | 4-phenylphenyl | 1.67 |
| 6 | H | H | 3-phenylphenyl | 1.67 |
| 7 | H | H | 4-phenoxyphenyl | 1.66 |
| 8 | H | H | 9H-fluoren-2-yl | 1.70 |
| 9 | H | H | 1,2-dihydroacenaphthylen-5-yl | 1.72 |
| 10 | H | H | dibenzofuran-2-yl | 1.72 |
| 11 | H | H | dibenzofuran-4-yl | 1.72 |
| 12 | H | H | dibenzothien-2-yl | 1.74 |
| 13 | H | H | dibenzothien-4-yl | 1.74 |
| 14 | H | H | 4-quinolinyl | 1.71 |
| 15 | H | H | 2-quinolinyl | 1.71 |
| 16 | H | H | 3-quinolinyl | 1.71 |
| 17 | H | H | 1-isoquinolinyl | 1.71 |
| 18 | H | H | 4-isoquinolinyl | 1.71 |
| 19 | H | H | 1H-indol-3-yl | 1.72 |
| 20 | H | H | 1H-pyrrol-2-yl | 1.69 |
| 21 | H | H | 1H-pyrrol-3-yl | 1.69 |
| 22 | H | H | 2-pyridyl | 1.68 |
| 23 | H | H | 3-pyridyl | 1.68 |
| 24 | H | H | 4-pyridyl | 1.68 |
| 25 | H | H | 5-pyrimidinyl | 1.68 |
| 26 | H | H | 2-cyanophenyl | 1.71 |
| 27 | H | H | 3-cyanophenyl | 1.71 |
| 28 | H | H | 4-cyanophenyl | 1.71 |
| 29 | H | H | 4-cyano-1-naphthyl | 1.74 |
| 30 | H | H | 5-cyano-1-naphthyl | 1.74 |
| 31 | H | H | 4-cyano-2-naphthyl | 1.74 |
| 32 | H | H | 6-cyano-2-naphthyl | 1.74 |
| 33 | Br | H | phenyl | 1.69 |
| 34 | Br | H | 1-naphthyl | 1.72 |
| 35 | Br | H | 2-naphthyl | 1.72 |
| 36 | Br | H | 9-phenanthryl | 1.74 |
| 37 | Br | H | 4-phenylphenyl | 1.69 |
| 38 | Br | H | 3-phenylphenyl | 1.69 |
| 39 | Br | H | 4-phenoxyphenyl | 1.69 |
| 40 | Br | H | 9H-fluoren-2-yl | 1.72 |
| 41 | Br | H | 1,2-dihydroacenaphthylen-5-yl | 1.73 |
| 42 | Br | H | dibenzofuran-2-yl | 1.74 |
| 43 | Br | H | dibenzofuran-4-yl | 1.74 |

TABLE A-continued

| # | $R^{x1}$ | $R^{x2}$ | Ar | $n_D$ (calc.) |
|---|---|---|---|---|
| 44 | Br | H | dibenzothien-2-yl | 1.75 |
| 45 | Br | H | dibenzothien-4-yl | 1.75 |
| 46 | Br | H | 4-quinolinyl | 1.72 |
| 47 | Br | H | 2-quinolinyl | 1.72 |
| 48 | Br | H | 3-quinolinyl | 1.72 |
| 49 | Br | H | 1-isoquinolinyl | 1.72 |
| 50 | Br | H | 4-isoquinolinyl | 1.72 |
| 51 | Br | H | 1H-indol-3-yl | 1.73 |
| 52 | Br | H | 1H-pyrrol-2-yl | 1.71 |
| 53 | Br | H | 1H-pyrrol-3-yl | 1.71 |
| 54 | Br | H | 2-pyridyl | 1.70 |
| 55 | Br | H | 3-pyridyl | 1.70 |
| 56 | Br | H | 4-pyridyl | 1.70 |
| 57 | Br | H | 5-pyrimidinyl | 1.70 |
| 58 | Br | H | 2-cyanophenyl | 1.74 |
| 59 | Br | H | 3-cyanophenyl | 1.74 |
| 60 | Br | H | 4-cyanophenyl | 1.74 |
| 61 | Br | H | 4-cyano-1-naphthyl | 1.77 |
| 62 | Br | H | 5-cyano-1-naphthyl | 1.77 |
| 63 | Br | H | 4-cyano-2-naphthyl | 1.77 |
| 64 | Br | H | 6-cyano-2-naphthyl | 1.77 |
| 65 | CN | H | phenyl | 1.72 |
| 66 | CN | H | 1-naphthyl | 1.74 |
| 67 | CN | H | 2-naphthyl | 1.74 |
| 68 | CN | H | 9-phenanthryl | 1.77 |
| 69 | CN | H | 4-phenylphenyl | 1.73 |
| 70 | CN | H | 3-phenylphenyl | 1.73 |
| 71 | CN | H | 4-phenoxyphenyl | 1.72 |
| 72 | CN | H | 9H-fluoren-2-yl | 1.75 |
| 73 | CN | H | 1,2-dihydroacenaphthylen-5-yl | 1.76 |
| 74 | CN | H | dibenzofuran-2-yl | 1.77 |
| 75 | CN | H | dibenzofuran-4-yl | 1.77 |
| 76 | CN | H | dibenzothien-2-yl | 1.78 |
| 77 | CN | H | dibenzothien-4-yl | 1.78 |
| 78 | CN | H | 4-quinolinyl | 1.75 |
| 79 | CN | H | 2-quinolinyl | 1.75 |
| 80 | CN | H | 3-quinolinyl | 1.75 |
| 81 | CN | H | 1-isoquinolinyl | 1.75 |
| 82 | CN | H | 4-isoquinolinyl | 1.75 |
| 83 | CN | H | 1H-indol-3-yl | 1.76 |
| 84 | CN | H | 1H-pyrrol-2-yl | 1.73 |
| 85 | CN | H | 1H-pyrrol-3-yl | 1.73 |
| 86 | CN | H | 2-pyridyl | 1.72 |
| 87 | CN | H | 3-pyridyl | 1.72 |
| 88 | CN | H | 4-pyridyl | 1.72 |
| 89 | CN | H | 5-pyrimidinyl | 1.72 |
| 90 | CN | H | 2-cyanophenyl | 1.72 |
| 91 | CN | H | 3-cyanophenyl | 1.72 |
| 92 | CN | H | 4-cyanophenyl | 1.72 |
| 93 | CN | H | 4-cyano-1-naphthyl | 1.75 |
| 94 | CN | H | 5-cyano-1-naphthyl | 1.75 |
| 95 | CN | H | 4-cyano-2-naphthyl | 1.75 |
| 96 | CN | H | 6-cyano-2-naphthyl | 1.75 |

In this subgroup (1c) of groups (1) and (5) of embodiments the structural unit of the formula (II) is a structural unit of the formula (IIa'):

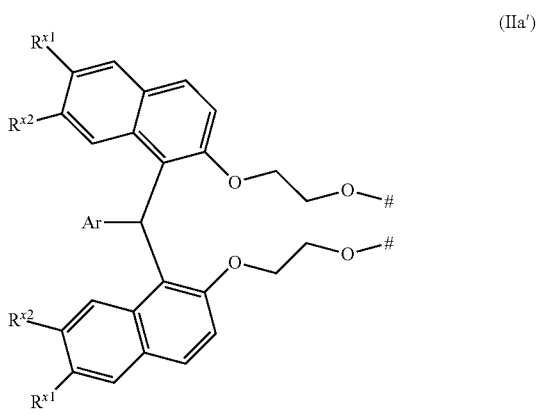

(IIa')

where # represents a connection point to a neighboring structural unit and where $R^{x1}$ and $R^{x2}$ are hydrogen or have one of the meanings, in particular the preferred meanings given for $R^x$ as defined herein and Ar is as defined herein and has in particular one of the preferred meanings. Examples of such structural units (IIa') are those, where the combination of Ar, $R^{x1}$ and $R^{x2}$ as defined in one row of table A.

The compounds of the formula (I) as well as precursors thereof can be prepared for example by the process depicted in the following reaction scheme 1, starting from the phenol derivative of the formula (VI) and the aryl aldehyde of the formula (VII) (compare for example: J. P. Poupelin et al., Eur. J. Med. Chem. 1978, 13(1), 67-71; A. Alizadeh et al., J. Iran. Chem. Soc., 2010, 7(2), 351-358; and J. P. Poupelin et al., Eur. J. Med. Chem. 1978, 13(4), 381-71):

Scheme 1

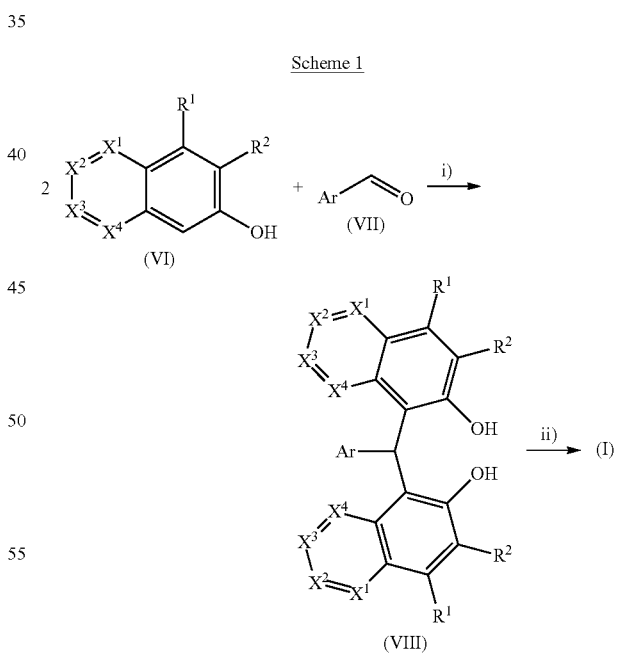

In scheme 1 the variables $R^1$, $R^2$, Ar, $X^1$, $X^2$, $X^3$ and $X^4$ are as defined herein.

In step i) of the process according to scheme 1, the phenol derivative (VI) and the aryl aldehyde (VII) undergo a condensation reaction in the presence of an acid catalyst to yield the diol of the formula (VIII). Suitable acids for catalyzing the reaction of step i) are generally strong acids, such as sulfuric acid, methanesulfonic acid and p-toluene-sulfonic acid, in particular methanesulfonic acid. The reaction is typically carried out in a polar organic solvent such as $C_2$-$C_6$-alkanols, such as isopropanol, and halogenated $C_1$-$C_4$-alkanes, such as dichloromethane, at a reaction temperature that is usually in the range of 0 to 60° C. and particularly in the range of 10 to 40° C.

In step ii) of scheme 1 the diol of formula (VIII) is reacted with a cyclic carbonate of the formula (IX),

(IX)

where Y is as defined above and in particular 1,2-ethandiyl, to yield the compound of formula (I). Hence, an example of a suitable compound of formula (IX) is ethylene carbonate. The compound of formula (IX) is usually applied in excess of the desired stoichiometry, i.e. the molar ratio of compound (IX) to the diol (VIII) exceeds 2:1 and is in particular in the range from 2.2:1 to 5:1. The reaction according to step ii) of scheme 1 is usually performed in the presence of a base, in particular an oxo base, especially an alkaline carbonate such as sodium carbonate or potassium carbonate. The base is usually used in catalytic amounts, e.g. in amount from 0.1 to 0.5 mol per 1 mol of the diol (VIII). Frequently, the reaction of the diol of formula (VIII) with the compound of formula (IX) is performed in an aprotic organic solvent, in particular in an aromatic hydrocarbon solvent such as toluene or xylene and mixtures thereof. The reaction according to step ii) of scheme 1 is usually performed at temperatures in the range from 50 to 150° C.

In case the variables $X^1$, $X^2$, $X^3$ and $X^4$ of the compound of the formula (I) include substituents $R^x$ that are bromine, a further step iii) may be added to the reaction sequence of scheme 1 in order to replace bromine atoms with substituents $R^x$ that are as defined above and are attached to the remainder of the molecule via an alkyl, alkenyl or a (het)aryl group. Examples of such substituents $R^x$ are $CH_3$, $CH=CH_2$, phenyl, naphthyl or pyridyl. In step iii) the compound of formula (I) is reacted with an boronic compound of the formula (X),

where $R^x$ is as defined above, provided that it is attached to the remainder of the molecule via an alkyl, alkenyl or a (het)aryl group, or, alternatively, reacted with an ester or anhydride of (X), in particular a $C_1$-$C_4$-alkyl ester of (X), in the presence of a transition metal catalyst, in particular in the presence of a palladium catalyst. Frequently, step iii) is performed under the conditions of a so-called "Suzuki Reaction" or "Suzuki Coupling" (see e.g. A. Suzuki et al., Chem. Rev. 1995, 95, 2457-2483; N. Zhe et al., J. Med. Chem. 2005, 48 (5), 1569-1609; Young et al., J. Med. Chem. 2004, 47 (6), 1547-1552; C. Slee et al., Bioorg. Med. Chem. Lett. 2001, 9, 3243-3253; T. Zhang et al., Tetrahedron Lett., 52 (2011), 311-313, S. Bourrain et al., Synlett. 5 (2004), 795-798, B. Li et al., Europ. J. Org. Chem. 20113932-3937). Suitable transition metal catalysts are in particular palladium compounds, which bear at least one palladium atom and at least one tri-substituted phosphine ligand. Examples of palladium catalysts are tetrakis(triphenylphosphine) palladium, tetrakis(tritolylphosphine) palladium and [1,1-bis(diphenylphosphino)ferro-cene]dichloropalladium(II) ($PdCl_2$(dppf)). Frequently, the palladium catalysts are prepared in situ from a suitable palladium precursor and a suitable phosphine ligand. Suitable palladium precursors are palladium compounds such as tris-(dibenzylideneacetone)dipalladium(0) ($Pd_2(dba)_3$) or palladium(II) acetate ($Pd(OAc)_2$). Suitable phosphine ligands are in particular tri(substituted) phosphines, e.g. a triaryl-phosphines such as triphenylphosphine, tritolylphosphine or 2,2'-bis(diphenyl-phosphino)-1, 1'-binaphthalene (BINAP), tri(cyclo)alkylphosphine such as tris-n-butylphosphine, tris(tert-butyl)phosphine or tris(cyclohexylphosphine), or dicyclohexyl-(2',4',6'-tri-iso-propyl-biphenyl-2-yl)-phosphane (X-Phos). Usually, the reaction is performed in the presence of a base, in particular an oxo base, such as an alkaline alkoxide, earth alkaline alkoxide, alkaline hydroxides, earth alkaline hydroxides, alkaline phosphates, earth alkaline phosphates, alkaline carbonates or earth alkaline carbonates such as or sodium ethoxide, sodium tert-butoxide, potassium tert-butoxide, lithium hydroxide, barium hydroxide, potassium phosphate, sodium carbonate, potassium carbonate, or cesium carbonate. Frequently, the reaction according to step iii) is performed in an organic solvent or in a mixture thereof with water. If the reaction is performed in a mixture of an organic solvent and water, the reaction mixture may be monophasic or biphasic. Suitable organic solvents include but are not limited to aromatic hydrocarbons such as toluene or xylene, acyclic and cyclic ethers, such as methyl tert.-butyl ether, ethyl tert.-butyl ether, diisopropylether, dioxane or tetrahydrofurane, ketones, such as 2-butanone, and aliphatic alcohols having 1 to 4 carbon atoms, such as methanol, ethanol or isopropanol, as well as mixtures thereof. The reaction according to step iii) is usually performed at temperatures in the range from 50 to 150° C.

Rather than subsequent to step ii), the conversion according to step iii) can alternatively be carried out after step i) and before step ii) of the reaction sequence depicted in scheme 1, i.e. instead of the sequence step i), step ii), step iii) the alternative sequence step i), step iii), step ii) is followed. It is also possible to start from a bromine containing naphthol type compound of the formula (VI), subjecting this compound to the conversion according to step iii) and then perform steps i) and ii) as outlined above.

If carried out in the alternative sequence step i), step iii), step ii), the reaction conditions for the individual reaction of steps i), ii) and iii) are the same or almost the same as described above for the sequence step i), step ii), step iii).

The reaction mixtures obtained in the individual steps i) to iii) are worked up in a conventional way, e.g. by mixing with water, separating the phases and, where appropriate, purifying the crude products by washing, chromatography or crystallization. The intermediates in some cases result in the form of colourless or pale brownish, viscous oils, which are freed of volatiles or purified under reduced pressure and at moderately elevated temperature. If the intermediates are obtained as solids, the purification can be achieved by recrystallization or washing procedures, such as slurry washing.

The compounds of the formulae (VI), (VII), (IX) and (X) are commercially available or can be prepared by methods known from the art.

As stated above, the compounds of the present invention can be obtained in high purity, which means that a product is obtained, which does not contain significant amounts of organic impurities different from the compound of formula (I), except for volatiles. Usually, the purity of compounds of formula (I) is at least 95%, in particular at least 98% and especially at least 99%, based on the non-volatile organic matter, i.e. the product contains at most 5%, in particular at most 2% and especially at most 1% of non-volatile impurities different from the compound of formula (I).

The term "volatiles" refers to organic compounds, which have a boiling point of less than 200° C. at standard pressure (105 Pa). Consequently, non-volatile organic matter is understood to mean compounds having a boiling point, which exceeds 200° C. at standard pressure.

It is a particular benefit of the invention that the compounds of formulae (I), (Ia), (Ia'), (Ib), (Ic), (Id), (Ie) and (If), and likewise their solvates, can often be obtained in crystalline form. In the crystalline form the compound of formula (I) may be present in pure form or in the form of a solvate with water or an organic solvent. Therefore, a particular aspect of the invention relates to the compounds of formula (I), which are essentially present in crystalline form. In particular, the invention relates to crystalline forms, where the compound of formula (I) is present without solvent and to the crystalline solvates of the compounds of formula (I), where the crystals contain a solvent incorporated.

It is a particular benefit of the invention that the compounds of the formulae (I), (Ia), (Ia'), (Ib), (Ic), (Id), (Ie) and (If), and likewise their solvates, can often be easily crystallized from conventional organic solvents. This allows for an efficient purification of the compounds of formula (I). Suitable organic solvents for crystallizing the compounds of the formula (I) or their solvates, include but are not limited to aromatic hydrocarbons such as toluene or xylene, aliphatic ketones in particular ketones having from 3 to 6 carbon atoms, such as acetone, methyl ethyl ketone, methyl isopropyl ketone or diethyl ketone, aliphatic and alicyclic ethers, such as diethyl ester, dipropyl ether, methyl isobutyl ether, methyl tert-butyl ether, ethyl tert-butyl ether, dioxane or tetrahydrofurane, and aliphatic alcohols having 1 to 4 carbon atoms, such as methanol, ethanol or isopropanol, as well as mixtures thereof.

Alternatively, the compounds of the formulae (I), (Ia), (Ia'), (Ib), (Ic), (Id), (Ie) and (If), and likewise their solvates, can be obtained in purified form by employing other simple and efficient methods for purifying the raw products of the compounds of the formula (I), such as in particular slurry washing the raw solids obtained directly after the conversion to prepare the compounds of formula (I). Slurry washing is typically conducted at ambient temperature or elevated temperatures of usually about 30 to 90° C., in particular 40 to 80° C. Suitable organic solvents here are in principle the same as those listed above as being suitable for crystallizing the compounds of formula (I), such as in particular the mentioned aromatic hydrocarbons, aliphatic ketones and aliphatic ethers, e.g. toluene, methyl ethyl ketone and methyl tert-butyl ether.

Accordingly, the compounds of formulae (I), (Ia), (Ia'), (Ib), (Ic), (Id), (Ie) and (If), respectively, used for the preparation of the thermoplastic polymers, in particular the polycarbonates, as defined herein, can be easily prepared and obtained in high yield and high purity. In particular, compounds of formulae (I), (Ia), (Ia'), (Ib), (Ic), (Id), (Ie) and (If), respectively, can be obtained in crystalline form, which allows for an efficient purification to the degree required in the preparation of optical resins. In particular, these compounds can be obtained in a purity which provides for high refractive indices and also low haze, which is particularly important for the use in the preparation of optical resins of which the optical devise is made of. In conclusion, the compounds of formulae (I), (Ia), (Ia'), (Ib), (Ic), (Id), (Ie) and (If), respectively, are particularly useful as monomers in the preparation of the optical resins.

A skilled person will readily appreciate that the formula (I) of the monomer used corresponds to the formula (II) of the structural unit comprised in the thermoplastic resin. Likewise, the formulae (Ia), (Ia'), (Ib), (Ic), (Id), (Ie) and (If), respectively, of the monomer used corresponds to the formulae (IIa), (IIa'), (IIb), (IIc), (IId), (IIe) and (IIf), respectively, of the structural unit comprised in the thermoplastic resin.

A skilled person will also appreciate that the structural units of the formulae (II), (IIa), (IIa'), (IIb), (IIc), (IId), (IIe) and (IIf) are repeating units within the polymer chains of the thermoplastic resin.

In addition to the structural units of the formulae (II), (Ia), (Ia'), (IIb), (IIc), (IId), (IIe) and (IIf), respectively, the thermoplastic resin may have structural units different therefrom. In a preferred embodiment, these further structural units are derived from aromatic monomers of the formula (IV) resulting in structural units of the formula (V):

$$HO-R^z-A^3-R^z-OH \quad (IV)$$

$$\#-O-R^z-A^3-R^z-O-\# \quad (V)$$

where
$A^3$ is a polycyclic radical bearing at least 2 benzene rings, wherein the benzene rings may be connected by A' and/or directly fused to each other and/or fused by a non-benzene carbocycle, where $A^3$ is unsubstituted or substituted by 1, 2 or 3 radicals $R^{aa}$, which are selected from the group consisting of halogen, $C_1$-$C_6$-alkyl, $C_5$-$C_6$-cycloalkyl and phenyl, in particular phenyl and methyl;

A' is selected from the group consisting of a single bond, O, C=O, S, $SO_2$, $CH_2$, CH—Ar", CHAr"$_2$, CH(CH$_3$), C(CH$_3$)$_2$ and a radical A"

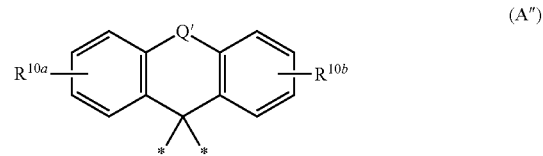

(A")

where
Q' represents a single bond, O, NH, C=O, CH$_2$ or CH=CH, in particular a single bond or C=O; and
$R^{10a}$, $R^{10b}$, independently of each other are selected from the group consisting of hydrogen, fluorine, CN, R, OR, $CH_kR_{3-k}$, $NR_2$, C(O)R and C(O)NH$_2$ and where $R^{10a}$, $R^{10b}$ are in particular hydrogen;

Ar" is selected from the group consisting of mono- or polycyclic aryl having from 6 to 26 carbon atoms and mono- or polycyclic hetaryl having a total of 5 to 26 atoms, which are ring members, where 1, 2, 3 or 4 of these atoms are selected from nitrogen, sulphur and oxygen, while the remainder of these atoms are carbon atoms, in particular phenyl or naphthyl, where Ar" is unsubstituted or substituted by 1, 2 or 3 radicals $R^{ab}$, which are selected from the group consisting of halogen, $C_1$-$C_6$-alkyl, $C_5$-$C_6$-cycloalkyl and phenyl, in particular phenyl and methyl;

$R^z$ is a single bond, $Alk^1$ or O-$Alk^2$-, where O is bound to $A^3$, and where $Alk^1$ is $C_2$-$C_4$-alkandiyl;
$Alk^2$ is $C_2$-$C_4$-alkandiyl, in particular linear alkandiyl having 2 to 4 carbon atoms and especially $CH_2CH_2$; and \# represents a connection point to a neighboring structural unit.

In the context of formulae (IV) and (V), $A^3$ is in particular a polycyclic radical bearing 2 benzene or naphthaline rings, wherein the benzene rings are connected by A'. In this context A' is in particular selected from the group consisting of a single bond, CH—Ar'', CHAr''$_2$, and a radical A''.

In the context of formulae (IV) and (V), $R^z$ is in particular O-Alk$^2$-, where Alk$^2$ is in particular linear alkandiyl having 2 to 4 carbon atoms and especially CH$_2$CH$_2$ Amongst the monomers of formula (IV) preference is given to monomers of the general formulae (IV-1) to (IV-8), where $R^z$ and $R^{aa}$ are as defined herein and $R^z$ is in particular selected from a single bond, CH$_2$ and OCH$_2$CH$_2$:

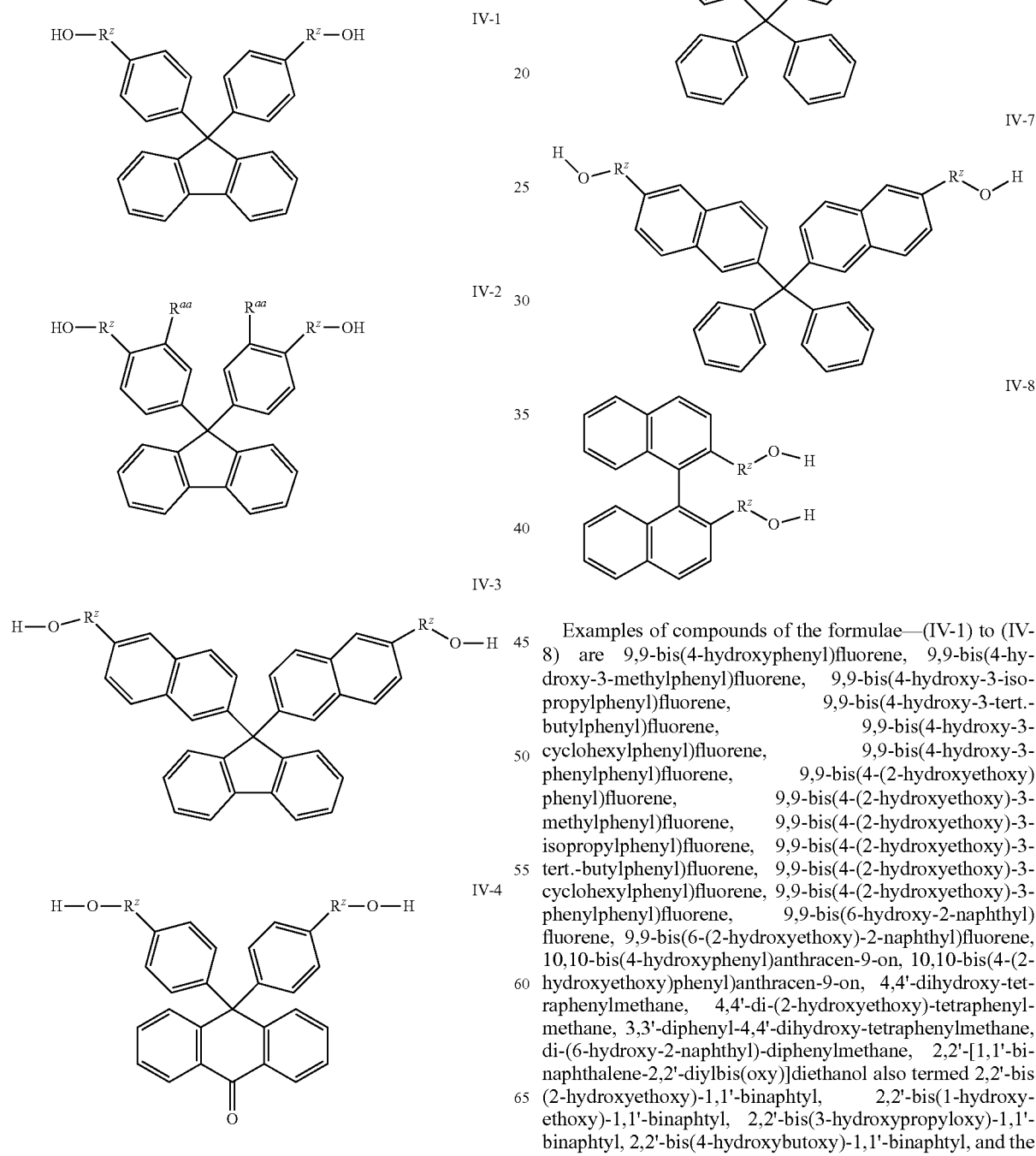

Examples of compounds of the formulae—(IV-1) to (IV-8) are 9,9-bis(4-hydroxyphenyl)fluorene, 9,9-bis(4-hydroxy-3-methylphenyl)fluorene, 9,9-bis(4-hydroxy-3-isopropylphenyl)fluorene, 9,9-bis(4-hydroxy-3-tert.-butylphenyl)fluorene, 9,9-bis(4-hydroxy-3-cyclohexylphenyl)fluorene, 9,9-bis(4-hydroxy-3-phenylphenyl)fluorene, 9,9-bis(4-(2-hydroxyethoxy)phenyl)fluorene, 9,9-bis(4-(2-hydroxyethoxy)-3-methylphenyl)fluorene, 9,9-bis(4-(2-hydroxyethoxy)-3-isopropylphenyl)fluorene, 9,9-bis(4-(2-hydroxyethoxy)-3-tert.-butylphenyl)fluorene, 9,9-bis(4-(2-hydroxyethoxy)-3-cyclohexylphenyl)fluorene, 9,9-bis(4-(2-hydroxyethoxy)-3-phenylphenyl)fluorene, 9,9-bis(6-hydroxy-2-naphthyl)fluorene, 9,9-bis(6-(2-hydroxyethoxy)-2-naphthyl)fluorene, 10,10-bis(4-hydroxyphenyl)anthracen-9-on, 10,10-bis(4-(2-hydroxyethoxy)phenyl)anthracen-9-on, 4,4'-dihydroxy-tetraphenylmethane, 4,4'-di-(2-hydroxyethoxy)-tetraphenylmethane, 3,3'-diphenyl-4,4'-dihydroxy-tetraphenylmethane, di-(6-hydroxy-2-naphthyl)-diphenylmethane, 2,2'-[1,1'-binaphthalene-2,2'-diylbis(oxy)]diethanol also termed 2,2'-bis(2-hydroxyethoxy)-1,1'-binaphtyl, 2,2'-bis(1-hydroxyethoxy)-1,1'-binaphtyl, 2,2'-bis(3-hydroxypropyloxy)-1,1'-binaphtyl, 2,2'-bis(4-hydroxybutoxy)-1,1'-binaphtyl, and the like. Among the monomers of the general formula (IV) or of formulae (IV-1) to (IV-8), particular preference is given to the monomers of formulae (IV-1), (IV-2), (IV-3) and (IV-8) with particular preference given to 2,2'-bis(2-hydroxyethoxy)-1,1'-binaphtyl, 9,9-bis(6-(2-hydroxyethoxy)-2-naphthyl)fluorene and 9,9-bis(4-(2-hydroxyethoxy)-3-phenylphenyl)fluorene.

Accordingly, amongst the structural units of formula (V) that may be comprised in the thermoplastic resin preference is given to monomers of the general formulae (V-1) to (V-8), where $R^z$ is as defined herein and is in particular selected from a single bond and $OCH_2CH_2$:

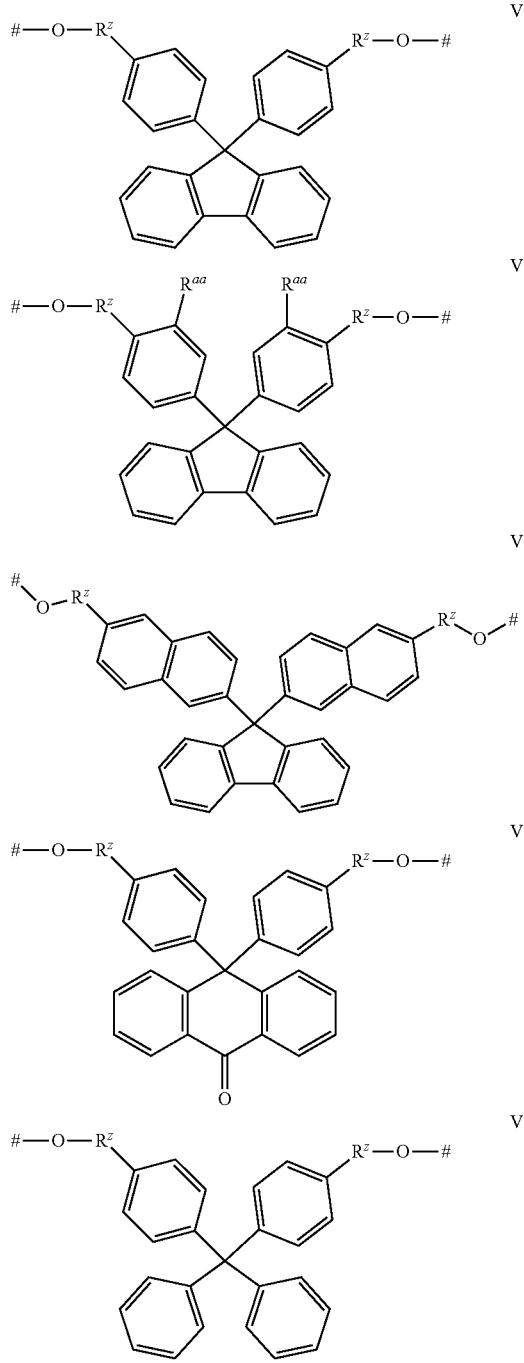

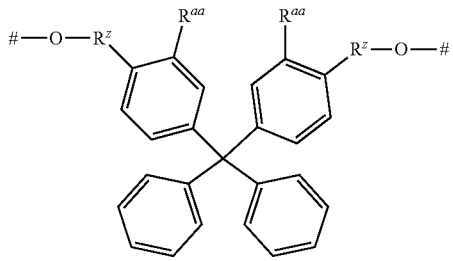

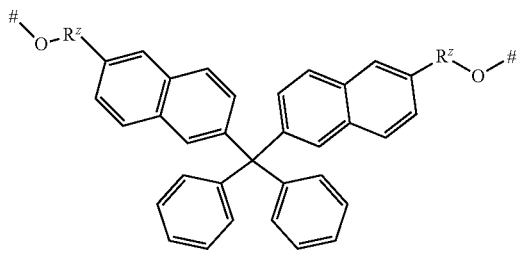

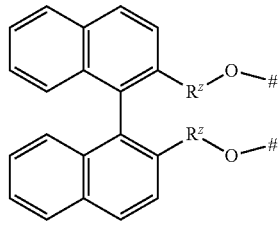

The monomers of formula (I) used for producing the thermoplastic resin may contain certain impurities resulting from their preparation, e.g. hydroxy compounds, which bear an OH group instead of a group —O—Y—OH. The total amount of such hydroxy compounds is preferably 1000 ppm or lower, more preferably 500 ppm or lower, still more preferably 200 ppm or lower, and especially preferably 100 ppm or lower. The total content of the impurities in the monomers used for preparing the thermoplastic resin is preferably 1000 ppm or lower.

Suitable thermoplastic resins for the preparation of optical devices, such as lenses and optical films, are in particular polycarbonates, polyestercarbonates and polyesters. Preferred thermoplastic resins for the preparation of optical devices, such as lenses and optical films, are in particular polycarbonates.

Said polycarbonates are structurally characterized by having structural units of at least one of the formulae (II), (IIa), (IIa'), (IIb), (IIc), (IId), (IIe) and (IIf), respectively, optionally structural units derived from diol monomers, which are different from the monomer compound of the formula (I), e.g. structural units of the formula (V),

—O—$R^z$-$A^3$-$R^z$—O-#     (V)

where
, $R^z$ and $A^3$ are as defined herein above;
and a structural unit of formula (ill-1) stemming from the carbonate forming component:

 (III-1)

where each # represents a connection point to a neighboring structural unit, i.e. to 0 at the connection point of the structural unit of the formula (II) and, if present, to 0 at the connection point of the structural unit of the formula (V).

Said polyesters are structurally characterized by having structural units of at least one of the formulae (II), (IIa), (IIa'), (IIb), (IIc), (IId), (IIe) and (IIf), respectively, optionally structural units derived from diol monomers which are different from the monomer compound of the formula (I), e.g. structural units of the formula (V), and structural units derived from dicarboxylic acid, e.g. of formula (III-2) in case of a benzene dicarboxylic acid, of formula (III-3) in case of a naphthalene carboxylic acid, of formula (III-4) in case of oxalic acid, of formula (III-5) in case of malonic acid and of formula III-6 in case of binaphthyl dicarboxylic acids, such as 2,2'-bis(hydroxycarbonylmethoxy)-1,1'-binaphthyl:

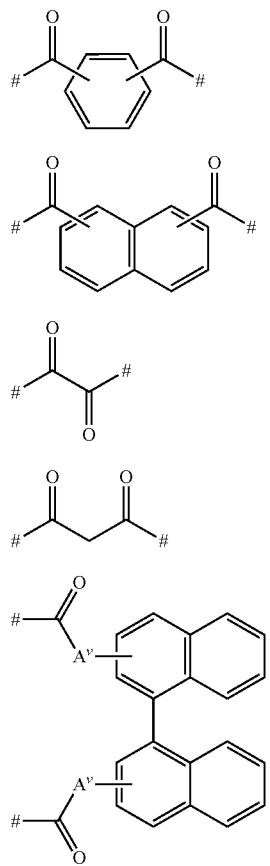

In formulae (III-2) to (III-6) each variable # represents a connection point to a neighboring structural unit, i.e. to O of the connection point of the structural unit of the formula (II) and, if present, to O of the connection point of the structural unit of the formula (V). In formula (III-6) the variable $A^v$ may be a single bond, $C_1$-$C_4$-alkylene or $C_1$-$C_4$-alkylene-O, such as $CH_2O$.

Said polyestercarbonates are structurally characterized by having structural units of at least one of the formulae (II), (IIa), (IIa'), (IIb), (IIc), (IId), (IIe) and (IIf), respectively, optionally structural units derived from diol monomers which are different from the monomer compound of the formula (I), e.g. structural units of the formula (V), a structural unit of formula (III-1) stemming from the carbonate forming component and structural units derived from dicarboxylic acid, e.g. of formula (III-2) in case of a benzene dicarboxylic acid, of formula (III-3) in case of a naphthalene carboxylic acid, of formula (III-4) in case of oxalic acid and of formula (III-5) in case of malonic acid.

A particular group of embodiments relates to thermoplastic copolymer resins, in particular polycarbonates, polyestercarbonates and polyesters, which have both structural units of formula (II) and one or more structural units of formula (V), i.e. resins, in particular polycarbonates, polyestercarbonates and polyesters, which are obtainable by reacting at least one monomer of formula (I) with one or more monomers of formula (IV). In this case the molar ratio of monomers of formula (I) to monomers of formula (IV) and likewise the molar ratio of the structural units of formula (II) to structural units of formula (V) are in the range from 5:95 to 80:20, in particular in the range from 10:90 to 70:30 and especially in the range from 15:85 to 60:40.

The thermoplastic copolymer resins of the present invention, such as a polycarbonate resin may include either one of a random copolymer structure, a block copolymer structure, and an alternating copolymer structure. The thermoplastic resin according to the present invention does not need to include all of structural units (II) and one or more different structural units (V) in one, same polymer molecule. Namely, the thermoplastic copolymer resin according to the present invention may be a blend resin as long as the above-described structures are each included in any of a plurality of polymer molecules. For example, the thermoplastic resin including all of structural units (II) and structural units (V) described above may be a copolymer including all of structural units (II) and structural units (V), it may be a mixture of a homopolymer or a copolymer including at least one structural unit (II) and a homopolymer or a copolymer including at least one structural unit (V) or it may be a blend resin of a copolymer including at least one structural unit (II) and a first structural unit (V) and a copolymer including at least one structural unit (II) and at least one other structural unit (V) different from the first structural units (V); etc.

Thermoplastic polycarbonates are obtainable by polycondensation of a diol component and a carbonate forming component. Similarly, thermoplastic polyesters and polyestercarbonates are obtainable by polycondensation of a diol component and a dicarboxylic acid, or an ester forming derivative thereof, and optionally a carbonate forming component.

The thermoplastic resin composition which includes a polycarbonate resin may contain, as impurities, phenol generated during the production of the polycarbonate resin, or carbonate diester or a material monomer remaining without being reacted. The concentration of the phenol in the thermoplastic resin composition is will generally not exceed 3000 ppm, in particular 2000 ppm and especially 1000 ppm and is frequently in the range from 0.1 to 3000 ppm, in particular 0.1 to 2000 ppm, and still more preferably 0.1 to 1000 ppm, 0.1 to 800 ppm, 0.1 to 500 ppm or 0.1 to 300 ppm. The concentration of the carbonate diester in the thermoplastic resin composition will generally not exceed 1000 ppm, in particular 500 ppm and especially 100 ppm and is frequently in the range from 0.1 to 1000 ppm, in particular 0.1 to 500 ppm, and especially 0.1 to 100 ppm. The concentration of the material monomer, i.e. monomers of the formula (I) and optionally (V) in the thermoplastic resin composition will generally not exceed 3000 ppm, in particular 2000 ppm and especially 1000 ppm and is frequently in the range from 0.1 to 3000 ppm, more preferably 0.1 to 2000 ppm, and especially preferably 1 to 1000 ppm.

The concentrations of the phenol and the carbonate diester in the thermoplastic resin composition may be adjusted to obtain a resin having properties suitable to the use thereof. The concentrations of the phenol, the carbonate diester, and the material monomer may be appropriately adjusted by changing the conditions or the device of polycondensation. Alternatively, the concentrations of the phenol and the carbonate diester may be adjusted by changing the conditions in an extrusion step after the polycondensation.

In the case where the concentration of the phenol or the carbonate diester is higher than the above-described range, a problem may occur that the strength of the resultant resin molded body is decreased or that an odor is generated, for example. By contrast, in the case where the concentrations of the phenol, the carbonate diester, or the material monomer may serve for a certain plasticity. Consequently, when their concentration is lower than the above-described ranges, the plasticity of the resin when the resin is melted may but be but not necessarily is undesirably decreased.

The weight-average molecular weight (Mw), as determined by GPC described below, of the thermoplastic resin according to the present invention is preferably in the range from 5000 to 100000 Dalton, more preferably 7500 to 80000 Dalton, and still more preferably 10000 to 70000 Dalton. The number-average molecular weight (Mn) of the thermoplastic resin according to the present invention is preferably 2000 to 20000, more preferably 2500 to 15000, and still more preferably 3000 to 14000.

The value of the molecular weight distribution (Mw/Mn) of the thermoplastic resin according to the present invention is preferably 1.0 to 15.0, more preferably 1.5 to 12.0, and still more preferably 2.0 to 9.5.

The above-mentioned polycarbonate resin has a high refractive index ($n_D$ or $n_d$) and thus is suitable to an optical lens. The values of the refractive index as referred herein are values of a film having a thickness of 0.1 mm may be measured by use of an Abbe refractive index meter by a method of JIS-K-7142. The refractive index of the polycarbonate resin according to the present invention at 23° C. at a wavelength of 589 nm is, in case the resin includes the structural unit (II), preferably 1.640 or higher, more preferably 1.650 or higher, still more preferably 1.660 or higher. For example, the refractive index of the copolycarbonate resin including the structural unit (II) and a structural unit (V) according to the present invention is preferably 1.640 to 1.690, preferably 1.650 to 1.690, still more preferably 1.660 to 1.690.

The Abbe number (v) of the polycarbonate resin is preferably 25 or lower, more preferably 23 or lower, and still more preferably 21 or lower. The Abbe number may be calculated by use of the following equation based on the refractive index at wavelengths of 487 nm, 589 nm and 656 nm at 23° C.

$$v=(n_D-1)/(n_F-n_C)$$

$n_D$: refractive index at a wavelength of 589 nm
$n_C$: refractive index at a wavelength of 656 nm
$n_F$: refractive index at a wavelength of 486 nm The glass transition temperature (Tg) of the polycarbonate resin as an example of the thermoplastic resin according to the present invention is, in consideration of that the polycarbonate is usable for injection molding, preferably 95 to 190° C., more preferably 130 to 180° C., and still more preferably 145 to 170° C. With regard to the molding fluidity and the molding heat resistance, the lower limit of Tg is preferably 135° C. and more preferably 140° C., and the upper limit of Tg is preferably 190° C. and more preferably 180° C. A glass transition temperature (Tg) in the above given ranges provides a significant range of usable temperature and avoids the risk that the melting temperature of the resin may be too high, and thus the resin may be undesirably decomposed or colored. What is more, it allows for preparing molds having a high surface accuracy.

An optical molded body such as an optical element produced by using a polycarbonate resin of the present invention has a total light transmittance of preferably 85% or higher, more preferably 87% or higher, and especially preferably 88% or higher. A total light transmittance of preferably 85% or higher is as good as that provided by bisphenol A type polycarbonate resin or the like.

The thermoplastic resin according to the present invention has high moisture and heat resistance. The moisture and heat resistance may be evaluated by performing a "PCT test" (pressure cooker test) on a molded body such as an optical element produced by use of the thermoplastic resin and then measuring the total light transmittance of the molded body after the PCT test. In the PCT test, first, an injection molded body having a diameter of 50 mm and a thickness of 3 mm is kept for 20 hours with PC305S III made by HIRAYAMA Corporation under the conditions of 120° C., 0.2 MPa, 100% RH for 20 hours. Then, the sample of the injection molded body is removed from the device and the total light transmittance is measured using the SE2000 type spectroscopic parallax measuring instrument made by Nippon Denshoku Industries Co., Ltd in accordance with the method of JIS-K-7361-1.

The thermoplastic resin according to the present invention has a post-PCT test total light transmittance of 60% or higher, preferably 70% or higher, more preferably 75% or higher, still more preferably 80% or higher, and especially preferably 85% or higher. As long as the total light transmittance is 60% or higher, the thermoplastic resin is considered to have a higher moisture and heat resistance than that of the conventional thermoplastic resin.

The thermoplastic resin according to the present invention has a b value, which represents the hue, of preferably 5 or lower. As the b value is smaller, the color is less yellowish, which is good as a hue.

According to the invention, the diol component, which is used in the preparation of the polycarbonates or polyesters, may additionally comprise one or more diol monomers, which are different from the monomer compound of the formula (I), such as one or more monomers of the formula (IV).

Suitable diol monomers, which are different from the monomer compound of the formula (I), are those, which are conventionally used in the preparation of polycarbonates, e.g.

aliphatic diols such as ethylene glycol, propanediol, butanediol, pentanediol and hexanediol;

alicyclic diols such as tricyclo[5.2.1.02,6]decane dimethanol, cyclohexane-1,4-dimethanol, decalin-2,6-dimethanol, norbornane dimethanol, pentacyclopentadecane dimethanol, cyclopentane-1,3-dimethanol, spiroglycol, 1,4:3,6-dianhydro-D-sorbitol, 1,4:3,6-dianhydro-D-mannitol and 1,4:3,6-dianhydro-L-iditol are also included in examples of the diol; and aromatic diols, in particular aromatic diols of the formula (IV), such as bis(4-hydrophenyl)methane, 1,1-bis(4-hydroxyphenyl)ethane, bis(4-hydroxyhenyl)ether, bis(4-hydroxyphenyl)sulfoxide, bis(4-hydroxyphenyl)sulfide, bis(4-hydroxyphenyl)sulfone, bis(4-hydroxyphenyl)ketone, 2,2-bis(4-hydroxyphenyl)propane, 2,2-bis(4-hydroxy-3-t-butylphenyl)propane, 2,2-bis(4-hydroxy-3-methylphenyl)propane, 1,1-bis(4-hydroxyphenyl)cyclopentane, 1,1-bis(4-hydroxyphenyl)cyclohexane, 2,2-bis(4-hydroxyphenyl) hexafluoro-propane, bis(4-hydroxyphenyl) diphenylmethane, 1,1-bis(4-hydroxyphenyl)-1-phenylethane, α,ω-bis[2-(p-hydroxyphenyl)ethyl] polydimethylsiloxane, α,ω-bis[3-(o-hydroxyphenyl) propyl]polydimethylsiloxane, 4,4'-[1,3-phenylenebis (1-methylethylidene)hydroxyphenyl]-1-phenylethane, 9,9-bis(4-hydroxyphenyl)fluorene, 9,9-bis[4-(2-hydroxyethoxy)-3-methylphenyl]fluorene, 9,9-bis[4-(2-hydroxyethoxy)-3-tert-butylphenyl]fluorene, 9,9-bis[4-(2-hydroxyethoxy)-3-isopropylphenyl]fluorene, 9,9-bis[4-(2-hydroxyethoxy)-3-cyclohexylphenyl] fluorene, 9,9-bis(4-hydroxy-3-methylphenyl)fluorene, 9,9-bis(4-hydroxy-3-phenylphenyl)fluorene, 9,9-bis(4-(2-hydroxyethoxy)phenyl)fluorene, 9,9-bis(4-(2-hydroxyethoxy)-3-phenylphenyl)fluorene, 9,9-bis(6-hydroxy-2-naphthyl)fluorene, 9,9-bis(6-(2-hydroxyethoxy)-2-naphthyl)fluorene, 10,10-bis(4-hydroxyphenyl)anthracen-9-on, 10,10-bis(4-(2-hydroxyethoxy)phenyl)anthracen-9-on and 2,2'-[1,1'-binaphthalene-2,2'-diylbis(oxy)]diethanol, also termed 2,2'-bis(2-hydroxyethoxy)-1,1'-binaphthyl or 2,2'-bis (2-hydroxyethoxy)-1,1'-binaphthalene (BNE).

Preferably, the diol component comprises at least one monomer of the formula (IV) in addition to the monomer of formula (I). In particular, the total amount of monomers of formulae (I) and (IV) contribute to the diol component by at least 90% by weight, based on the total weight of the diol component or by at least 90 mol-%, based on the total molar amount of the diol monomers of the diol component. In particular, the diol component comprises at least one monomer selected from the monomers of formulae (IV-1) to (IV-8) in addition to the monomer of formula (I). More particularly, the diol component comprises at least one monomer selected from the monomers of formulae (IV-1), (IV-2), (IV-3) and (IV-8) in addition to the monomer of formula (I). Especially, the diol component comprises at least one monomer selected from 2,2'-bis(2-hydroxyethoxy)-1,1'-2,2'-bis(2-hydroxyethoxy)-1,1'-binaphtyl, 9,9-bis(6-(2-hydroxyethoxy)-2-naphthyl)fluorene 9,9-bis(4-(2-hydroxyethoxy)-3-phenylphenyl)-fluorene and 9,9-bis(4-(2-hydroxyethoxy)-3-phenylphenyl)fluorene and combinations thereof in addition to the monomer of formula (I).

Frequently, the relative amount of monomer compound of formula (I), based on the total weight of the diol component, is at least 5% by weight, in particular at least 10% by weight, especially at least 15% by weight, preferably in the range of 5 to 90% by weight, in particular in the range of 10 to 80% by weight, especially in the range of 15 to 70% by weight, but may also be as high as 100% by weight.

Frequently, the relative molar amount of monomer compound of formula (I), based on the total molar of the diol component, is at least 5 mol-%, in particular at least 10 mol-% and especially at least 15 mol-%, preferably in the range of 5 to 80 mol-%, in particular in the range of 10 to 70 mol-%, especially in the range of 15 to 60 mol-%, but may also be as high as 100 mol-%.

Consequently, the relative molar amount of monomer compound of formula (IV), based on the total molar of the diol component, will typically not exceed 95 mol-%, in particular not exceed 90 mol-% and especially not exceed 85 mol-%, and is preferably in the range of 20 to 95 mol-%, in particular in the range of 30 to 90 mol-%, especially in the range of 40 to 85 mol-%, but may also be as high as 99.9 mol-%.

Frequently, the total molar amount of monomers of formula (I) and monomers of formula (IV) is at least 80 mol-%, in particular at least 90 mol-%, especially at least 95 mol-% or up to 100 mol-%, based on the total molar amount of the diol monomers in the diol component.

Examples of further preferred aromatic dihydroxy compounds, which can be used in addition to the monomers of formula (I) and optionally monomers of formula (IV) include, but are not limited to bisphenol A, bisphenol AP, bisphenol AF, bisphenol B, bisphenol BP, bisphenol C, bisphenol E, bisphenol F, bisphenol G, bisphenol M, bisphenol S, bisphenol P, bisphenol PH, bisphenol TMC, bisphenol Z and the like.

In order to adjust the molecular weight and the melt viscosity, the monomers forming the thermoplastic polymer may also include a monofunctional compound, in case of polycarbonates a monofunctional alcohol and in case of polyesters a monofunctional alcohol or a monofunctional carboxylic acid. Suitable monoalcohols are butanol, hexanol and octanol. Suitable monocarboxylic acids include e.g. benzoic acid, propionic acid and butyric acid. In order to increase the molecular weight and the melt viscosity, the monomers forming the thermoplastic polymer may also include a polyfunctional compound, in case of polycarbonates a polyfunctional alcohol having three or more hydroxyl groups and in case of polyesters a polyfunctional alcohol having three or more hydroxyl groups or a polyfunctional carboxylic acid having three or more carboxyl groups. Suitable polyfunctional alcohols are e.g. glycerine, trimethylol propane, pentaerythrit and 1,3,5-trihydroxy pentane. Suitable polyfunctional carboxylic acids having three or more carboxyl groups are e.g. trimellitic acid and pyromellitic acid. The total amount of these compounds, will frequently not exceed 10 mol-%, based on the molar amount of the diol component.

Suitable carbonate forming monomers, are those, which are conventionally used as carbonate forming monomers in the preparation of polycarbonates, include, but are not limited to phosgene, diphosgene and diester carbonates such as diethyl carbonate, diphenyl carbonate, di-p-tolyl carbonate, phenyl-p-tolyl carbonate, di-p-chlorophenyl carbonate and dinaphthyl carbonate. Out of these, diphenyl carbonate is particularly preferred. The carbonate forming monomer is frequently used at a ratio of 0.97 to 1.20 mol, and more preferably 0.98 to 1.10 mol, with respect to 1 mol of the dihydroxy compound(s) in total.

Suitable dicarboxylic acids include, but are not limited to
aliphatic dicarboxylic acids such as oxalic acid, malonic acid, succinic acid, glutaric acid, adipic acid, pimelic acid, suberic acid, azelaic acid;
alicyclic dicarboxylic acids such as tricyclo[5.2.1.02,6] decane dicarboxylic acid, cyclohexane-1,4-dicarboxylic acid, decalin-2,6-dicarboxylic acid, and norbornandicarboxylic acid; and
aromatic dicarboxylic acids, such as benzene dicarboxylic acids, specifically phthalic acid, isophthalic acid, 2-methylterephthalic acid or terephthalic acid, and naphthalene dicarboxylic acids, specifically naphthalene-1,3-dicarboxylic acid, naphthalene-1,4-dicarboxylic acid, naphthalene-1,5-dicarboxylic acid, naphthalene-1,6-dicarboxylic acid, naphthalene-1,7-dicarboxylic acid, naphthalene-2,5-dicarboxylic acid, naphthalene-2,6-dicarboxylic acid, naphthalene-2,7-dicarboxylic acid and binaphthyl dicarboxylic acids, such as 2,2'-bis(hydroxycarbonylmethoxy)-1,1'-binaphthyl.

Suitable ester forming derivatives of dicarboxylic acids include, but are not limited to the dialkyl esters, the diphenyl esters and the ditolyl esters.

In case of polyesters, the ester forming monomer is frequently used at a ratio of 0.97 to 1.20 mol, and more preferably 0.98 to 1.10 mol, with respect to 1 mol of the dihydroxy compound(s) in total.

The polycarbonates of the present invention can be prepared by reacting a diol component comprising a monomer of formula (I) and optionally a further diol monomer such as a monomer of the formula (IV) and a carbonate forming monomer by analogy to the well known preparation of polycarbonates as described e.g. in U.S. Pat. No. 9,360,593, US 2016/0319069 and US 2017/0276837, to which full reference is made.

The polyesters of the present invention can be prepared by reacting a diol component comprising a monomer of formula (I) and optionally a further diol monomer such as a monomer of the formula (IV) and a dicarboxylic acid or its ester forming derivative by analogy to the well known preparation of polyesters as described e.g. in US 2017/044311 and the references cited therein, to which full reference is made.

The polyestercarbonates of the present invention can be prepared by reacting a diol component comprising a monomer of formula (I) and optionally a further diol monomer such as a monomer of the formula (IV), a carbonate forming monomer and a dicarboxylic acid or its ester forming derivative by analogy to the well known preparation of polyestercarbonates as described in the art.

The polycarbonates, polyesters and polyestercarbonates are usually prepared by reacting the monomers of the diol component with the carbonate forming monomers and/or the ester forming monomers, i.e. the dicarboxylic acids or the ester forming derivatives thereof, in the presence of an esterification catalyst, in particular a transesterification catalyst, in case a carbonate forming monomer or an ester forming derivative of a polycarboxylic acid is used.

Suitable transesterification catalysts are basic compounds, which specifically include but are not limited to alkaline metal compounds, alkaline earth metal compound, nitrogen-containing compounds, and the like. Likewise, suitable transesterification catalysts are acidic compounds, which specifically include but are not limited to Lewis acid compounds of polyvalent metals, including compounds of as zinc, tin, titanium, zirconium, lead, and the like.

Examples of suitable alkaline metal compound include alkaline metal salts of an organic acid such as acetic acid, stearic acid, benzoic acid, or phenylphorsphoric acid, alkaline metal phenolates, alkaline metal oxides, alkaline metal carbonates, alkaline metal borohydrides, alkaline metal hydrogen carbonates, alkaline metal phosphate, alkaline metal hydrogenphosphate, alkaline metal hydroxides, alkaline metal hydrides, alkaline metal alkoxides, and the like. Specific examples thereof include sodium hydroxide, potassium hydroxide, cesium hydroxide, lithium hydroxide, sodium hydrogen carbonate, sodium carbonate, potassium carbonate, cesium carbonate, lithium carbonate, sodium acetate, potassium acetate, cesium acetate, lithium acetate, sodium stearate, potassium stearate, cesium stearate, lithium stearate, sodium borohydride, sodium borophenoxide, sodium benzoate, potassium benzoate, cesium benzoate, lithium benzoate, disodium hydrogen phosphate, dipotassium hydrogen phosphate, dilithium hydrogen phosphate, and disodium phenylphosphate; and also include disodium salt, dipotassium salt, dicesium salt, dilithium salt of bisphenol A, sodium salt, potassium salt, cesium salt and lithium salt of phenol; and the like.

Examples of the alkaline earth metal compound include alkaline earth metal salts of an organic acid such as acetic acid, stearic acid, benzoic acid, or phenylphorsphoric acid, alkaline earth metal phenolates, alkaline earth metal earth oxides, alkaline earth metal carbonates, alkaline metal borohydrides, alkaline earth metal hydrogen carbonates, alkaline earth metal hydroxides, alkaline earth metal hydrides, alkaline earth metal alkoxides, and the like. Specific examples thereof include magnesium hydroxide, calcium hydroxide, strontium hydroxide, barium hydroxide, magnesium hydrogen carbonate, calcium hydrogen carbonate, strontium hydrogen carbonate, barium hydrogen carbonate, magnesium carbonate, calcium carbonate, strontium carbonate, barium carbonate, magnesium acetate, calcium acetate, strontium acetate, barium acetate, magnesium stearate, calcium stearate, calcium benzoate, magnesium phenylphosphate, and the like.

Examples of the nitrogen-containing compound include quaternary ammoniumhydroxide, salt thereof, amines, and the like. Specific examples thereof include quaternary ammoniumhydroxides including an alkyl group, an aryl group or the like, such as tetramethylammoniumhydroxide, tetraethylammoniumhydroxide, tetrapropylammoniumhydroxide, tetrabutylammoniumhydroxide, trimethylbenzylammoniumhydroxide, and the like; tertiary amines such as triphenylamine, dimethylbenzylamine, triphenylamine, and the like; secondary amines such as diethylamine, dibutylamine, and the like; primary amines such as propylamine, butylamine, and the like; imidazoles such as 2-methylimidazole, 2-phenylimidazole, benzoimidazole, and the like; bases or basic salts such as ammonia, tetramethylammoniumborohydride, tetrabutylammoniumborohydride, tetrabutylammoniumtetraphenylborate, tetraphenylammoniumtetraphenylborate, and the like.

Preferred examples of the transesterification catalyst include salts of polyvalent metals such as zinc, tin, titanium, zirconium, lead, and the like, in particular the chlorides, alkoxyides, alkanoates, benzoates, acetylacetonates and the like. They may be used independently or in a combination of two or more. Specific examples of such transesterification catalyst include zinc acetate, zinc benzoate, zinc 2-ethylhexanoate, tin chloride (II), tin chloride (IV), tin acetate (II), tin acetate (IV), dibutyltinlaurate, dibutyltinoxide, dibutyltinmethoxide, zirconiumacetylacetonate, zirconium oxyacetate, zirconiumtetrabutoxide, lead acetate (II), lead acetate (IV), and the like.

The transesterification catalyst are frequently used at a ratio of $10^{-9}$ to $10^{-3}$ mol, preferably $10^{-7}$ to $10^{-4}$ mol, with respect to 1 mol of the dihydroxy compound(s) in total.

Frequently, the polycarbonates, polyesters and polyestercarbonates are prepared by a melt polycondensation method. In the melt polycondensation the monomers are reacted in the absence of an additional inert solvent. While the reaction is performed any byproduct formed in the transesterification reaction is removed by heating the reaction mixture at ambient pressure or reduced pressure.

The melt polycondensation reaction preferably comprises charging the monomers and catalyst into a reactor and subjecting the reaction mixture to conditions, where the reaction between the monomers and the formation of the byproduct takes place. It has been found advantages, if the byproduct resides for at least a while in the polycondensation reaction. However, in order to drive the polycondensation reaction to the product side, it is beneficial to remove at least a portion of the formed byproduct during or preferably at the end of the polycondensation reaction. In order to allow the byproduct in the reaction mixture, the pressure may be controlled by closing the reactor, or by increasing or decreasing the pressure. The reaction time for this step is 20 minutes or longer and 240 minutes or shorter, preferably 40 minutes or longer and 180 minutes or shorter, and especially preferably 60 minutes or longer and 150 minutes or shorter. In this step, in the case where the byproduct is removed by distillation soon after being generated, the finally obtained thermoplastic resin has a low content of high molecular-weight resin molecules. By contrast, in the case where the byproduct is allowed to reside in the reactor for a certain time, the finally obtained thermoplastic resin has a high content of high molecular-weight resin molecules.

The melt polycondensation reaction may be performed in a continuous system or in a batch system. The reactor usable for the reaction may be of a vertical type including an anchor-type stirring blade, a Maxblend® stirring blade, a helical ribbon-type stirring blade or the like; of a horizontal type including a paddle blade, a lattice blade, an eye glass-type blade or the like; or an extruder type including a screw. A reactor including a combination of such reactors is preferably usable in consideration of the viscosity of the polymerization product.

According to the method for producing the thermoplastic resin, such as a polycarbonate resin, after the polymerization reaction is finished, the catalyst may be removed or deactivated in order to maintain the thermal stability and the hydrolysis stability. A preferred method for deactivating the catalyst is the addition of an acidic substance. Specific examples of the acidic substance include esters such as butyl benzoate and the like; aromatic sulfonates such as p-toluenesulfonic acid and the like; aromatic sulfonic acid esters such as butyl p-toluenesulfonate, hexyl p-toluenesulfonate, and the like; phosphoric acids such as phosphorous acid, phosphoric acid, phosphonic acid, and the like; phosphorous acid esters such as triphenyl phosphite, monophenyl phosphite, diphenyl phosphite, diethyl phosphite, di-n-propyl phosphite, di-n-butyl phosphite, di-n-hexyl phosphite, dioctyl phosphite, monooctyl phosphite, and the like; phosphoric acid esters such as triphenyl phosphate, diphenyl phosphate, monophenyl phosphate, dibutyl phosphate, dioctyl phosphate, monooctyl phosphate, and the like; phosphonic acids such as diphenyl phosphonic acid, dioctyl phosphonic acid, dibutyl phosphonic acid, and the like; phosphonic acid esters such as diethyl phenylphosphonate, and the like; phosphines such as triphenylphosphine, bis(diphenylphosphino)ethane, and the like; boric acids such as boric acid, phenylboric acid, and the like; aromatic sulfonic acid salts such as tetarabutylphosphonium dodecylbenzensulfonate salt, and the like; organic halides such as chloride stearate, benzoyl chloride, chloride p-toluenesulfonate, and the like; alkylsulfonic acids such as dimethylsulfonic acid, and the like; organic halides such as benzyl chloride, and the like. These deactivators are frequently used at 0.01 to 50 mol, preferably 0.3 to 20 mol, with respect to the catalyst. After the catalyst has been deactivated, there may be a step of removing low boiling point compounds from the polymer by distillation. The distillation is preferably performed at reduced pressure, e.g. at a pressure of 0.1 to 1 mmHg at a temperature of 200 to 350° C. For this step, a horizontal device including a stirring blade having a high surface renewal capability such as a paddle blade, a lattice blade, an eye glass-type blade or the like, or a thin film evaporator is preferably used.

It is desirable that the thermoplastic resin such as a polycarbonate resin has a very small amount of foreign objects. Therefore, the molten product is preferably filtered to remove solids from the melt. The mesh of the filter is preferably 5 µm or less, and more preferably 1 µm or less. It is preferred that the generated polymer is filtrated by a polymer filter. The mesh of the polymer filter is preferably 100 µm or less, and more preferably 30 µm or less. A step of sampling a resin pellet needs to be performed in a low dust environment, needless to say. The dust environment is preferably of class 6 or lower, and more preferably of class 5 or lower.

The thermoplastic resin may be molded by any conventional molding procedure for producing optical elements. Suitable molding procedures include but are not limited to injection molding, compression molding, casting, roll processing, extrusion molding, extension and the like.

While it is possible to mold the thermoplastic resin of the invention as such, it is also possible to mold a resin composition, which contains at least one thermoplastic resin of the invention and which further contains at least one additive and/or further resin.

Suitable additives include antioxidants, processing stabilizers, photostabilizers, polymerization metal deactivators, flame retardants, lubricants, antistatic agents, surfactants, antibacterial agents, releasing agents, ultraviolet absorbers, plasticizers, compatibilizers, and the like. Suitable further resins are e.g. another polycarbonate resin, polyester carbonate resin, polyester resin and the like, which does not contain repeating units of the formula (I).

Examples of the antioxidant include but are not limited to triethyleneglycol-bis[3-(3-tert-butyl-5-methyl-4-hydroxyphenyl)propionate], 1,6-hexanediol-bis[3-(3,5-di-tert-butyl-4-hydroxyphenyl)propionate], pentaerythritol-tetrakis[3-(3,5-di-tert-butyl-4-hydroxyphenyl)propionate], octadecyl-3-(3,5-di-tert-butyl-4-hydroxyphenyl)propionate, 1,3,5-trimethyl-2,4,6-tris(3,5-di-tert-butyl-4-hydroxybenzyl)benzene, N,N-hexamethylenebis(3,5-di-tert-butyl-4-hydroxy-hydrocinnamide, 3,5-di-tert-butyl-4-hydroxybenzylphosphonate-diethylester, tris(3,5-di-tert-butyl-4-hydroxybenzyl)isocyanurate, and 3,9-bis{1,1-dimethyl-2-[β-(3-tert-butyl-4-hydroxy-5-methylphenyl)propionyloxy]ethyl}-2,4,8,10-tetraoxaspiro(5,5)undecane, and the like.

The content of the antioxidant in the thermoplastic resin is preferably 0.001 to 0.3 parts by weight with respect to 100 parts by weight of the thermoplastic resin.

Examples of the processing stabilizer include but are not limited to phosphorus-based processing stabilizers, sulfur-based processing stabilizers, and the like. Examples of the phosphorus-based processing stabilizer include phosphorous acid, phosphoric acid, phosphonous acid, phosphonic acid, esters thereof, and the like. Specific examples thereof include triphenylphosphite, tris(nonylphenyl)phosphite, tris(2,4-di-tert-butylphenyl)phosphite, tris(2,6-di-tert-butylphenyl)phosphite, tridecylphosphite, trioctylphosphite, trioctadecylphosphite, didecylmonophenylphosphite, dioctylmonophenylphosphite, diisopropylmonophenylphosphite, monobutyl-diphenylphosphite, monodecyldiphenylphosphite, monooctyldiphenylphosphite, bis(2,6-di-tert-butyl-4-methylphenyl)pentaerythritoldiphosphite, 2,2-methylenebis(4,6-di-tert-butylphenyl)octylphosphite, bis(nonylphenyl)pentaerythritoldiphosphite, bis(2,4-dicumylphenyl)pentaerythritoldiphosphite, bis(2,4-di-tert-butylphenyl)pentaerythritol-diphosphite, distearylpentaerythritoldiphosphite, tributylphosphate, triethylphosphate, trimethylphosphate, triphenylphosphate, diphenylmonoorthoxenylphosphate, dibutylphosphate, dioctylphosphate, diisopropylphosphate, dimethyl benzenephosphonate, diethyl benzenephosphonate, dipropyl benzenephosphonate, tetrakis(2,4-di-t-butylphenyl)-4,4'-biphenylenediphosphonite, tetrakis(2,4-di-t-butylphenyl)-4,3'-biphenylenediphosphonite, tetrakis(2,4-di-t-butylphenyl)-3,3'-biphenylenediphosphonite, bis(2,4-di-tert-butylphenyl)-4-phenyl-phenylphosphonite, bis(2,4-di-tert-butylphenyl)-3-phenyl-phenylphosphonite, and the like. The content of the phosphorus-based processing stabilizer in the thermoplastic resin composition is preferably 0.001 to 0.2 parts by weight with respect to 100 parts by weight of the thermoplastic resin.

Examples of the sulfur-based processing stabilizer include but are not limited to pentaerythritol-tetrakis(3-laurylthiopropionate), pentaerythritol-tetrakis(3-myristylthiopropionate), pentaerythritol-tetrakis(3-stearylthiopropionate), dilauryl-3,3'-thiodipropionate, dimyristyl-3,3'-thiodipropionate, distearyl-3,3'-thiodipropionate, and the like. The content of the sulfur-based processing stabilizer in the thermoplastic resin composition is preferably 0.001 to 0.2 parts by weight with respect to 100 parts by weight of the thermoplastic resin.

Preferred releasing agents contain at least 90% by weight of an ester of an alcohol and a fatty acid. Specific examples of the ester of an alcohol and a fatty acid include an ester of a monovalent alcohol and a fatty acid, and a partial ester or a total ester of a polyvalent alcohol and a fatty acid. Preferred examples of the above-described ester of an alcohol and a fatty acid include the esters of a monovalent alcohol having a carbon number of 1 to 20 and a saturated fatty acid having a carbon number of 10 to 30. Preferred examples of partial or total esters of a polyvalent alcohol and a fatty acid include the partial or total ester of a polyvalent alcohol having a carbon number of 2 to 25 and a saturated fatty acid having a carbon number of 10 to 30. Specific examples of the ester of a monovalent alcohol and a fatty acid include stearyl stearate, palmityl palmitate, butyl stearate, methyl laurate, isopropyl palmitate, and the like. Specific examples of the partial or total ester of a polyvalent alcohol and a fatty acid include monoglyceride stearate, monoglyceride stearate, diglyceride stearate, triglyceride stearate, monosorbitate stearate, monoglyceride behenate, monoglyceride caprylate, monoglyceride laurate, pentaerythritol monostearate, pentaerythritol tetrastearate, pentaerythritol tetrapelargonate, propyleneglycol monostearate, biphenyl biphenate, sorbitan monostearate, 2-ethylhexyl-stearate, total or partial esters of dipentaerythritol such as dipentaerythritol hexastearate and the like, etc. The content of the releasing agent in the resin composition is preferably 0.005 to 2.0 parts by weight, more preferably 0.01 to 0.6 parts by weight, and still more preferably 0.02 to 0.5 parts by weight, with respect to 100 parts by weight of the thermoplastic resin.

Preferred ultraviolet absorbers are selected from the group consisting of benzotriazole-based ultraviolet absorbers, benzophenone-based ultraviolet absorbers, triazine-based ultraviolet absorbers, cyclic iminoester-based ultraviolet absorbers, and cyanoacrylate-based ultraviolet absorbers. Namely, the following ultraviolet absorbers may be used independently or in a combination of two or more.

Examples of benzotriazole-based ultraviolet absorbers include 2-(2-hydroxy-5-methylphenyl)benzotriazole, 2-(2-hydroxy-5-tert-octylphenyl)benzotriazole, 2-(2-hydroxy-3,5-dicumylphenyl)phenylbenzotriazole, 2-(2-hydroxy-3-tert-butyl-5-methylphenyl)-5-chlorobenzotriazole, 2,2'-methylenebis[4-(1,1,3,3-tetramethylbutyl)-6-(2N-benzotriazole-2-yl)phenol)], 2-(2-hydroxy-3,5-di-tert-butylphenyl)benzotriazole, 2-(2-hydroxy-3,5-di-tert-butylphenyl)-5-chlorobenzotriazole, 2-(2-hydroxy-3,5-di-tert-amylphenyl)benzotriazole, 2-(2-hydroxy-5-tert-octylphenyl)benzotriazole, 2-(2-hydroxy-5-tert-butylphenyl) benzotriazole, 2-(2-hydroxy-4-octoxyphenyl)benzotriazole, 2,2'-methylenebis(4-cumyl-6-benzotriazolephenyl), 2,2'-p-phenylenebis(1,3-benzoxazine-4-one), 2-[2-hydroxy-3-(3,4,5,6-tetrahydrophthalimidemethyl)-5-methylphenyl]benzotriazole, and the like.

Examples of benzophenone-based ultraviolet absorbers include 2,4-dihydroxybenzophenone, 2-hydroxy-4-methoxybenzophenone, 2-hydroxy-4-octoxybenzophenone, 2-hydroxy-4-benzyloxybenzophenone, 2-hydroxy-4-methoxy-5-sulfoxybenzophenone, 2-hydroxy-4-methoxybenzophenone-5-sulfonic acid hydrate, 2,2'-dihydroxy-4-methoxybenzophenone, 2,2',4,4'-tetrahydroxybenzophenone, 2,2'-dihydroxy-4,4'-dimethoxybenzophenone, 2,2'-dihydroxy-4,4'-dimethoxy-5-sodiumsulfoxybenzophenone, bis(5-benzoyl-4-hydroxy-2-methoxyphenyl)methane, 2-hydroxy-4-n-dodecyloxybenzophenone, 2-hydroxy-4-methoxy-2'-carboxybenzophenone, and the like.

Examples of triazine-based ultraviolet absorbers include 2-(4,6-diphenyl-1,3,5-triazine-2-yl)-5-([(hexyl)oxy]-phenol, 2-(4,6-bis(2,4-dimethylphenyl)-1,3,5-triazine-2-yl)-5-([(octyl)oxy]-phenol, and the like.

Examples of cyclic iminoester-based ultraviolet absorbers include 2,2'-bis(3,1-benzoxazine-4-one), 2,2'-p-phenylenebis(3,1-benzoxazine-4-one), 2,2'-m-phenylenebis(3,1-benzoxazine-4-one), 2,2'-(4,4'diphenylene)bis(3,1-benzoxazine-4-one), 2,2'-(2,6-naphthalene)bis(3,1-benzoxazine-4-one), 2,2'-(1,5-naphthalene)bis(3,1-benzoxazine-4-one), 2,2'-(2-methyl-p-phenylene)bis(3,1-benzoxazine-4-one), 2,2'-(2-nitro-p-phenylene)bis(3,1-benzoxazine-4-one), 2,2'-(2-chloro-p-phenylene)bis(3,1-benzoxazine-4-one), and the like.

Examples of cyanoacrylate-based ultraviolet absorbers include 1,3-bis-[(2'-cyano-3',3'-diphenylacryloyl)oxy]-2,2-bis[(2-cyano-3,3-diphenylacryloyl)oxy]methyl)propane, 1,3-bis-[(2-cyano-3,3-diphenylacryloyl)oxy]benzene, and the like.

The content of the ultraviolet absorber in the resin composition is preferably 0.01 to 3.0 parts by weight, more preferably 0.02 to 1.0 parts by weight, and still more preferably 0.05 to 0.8 parts by weight, with respect to 100 parts by weight of the thermoplastic resin. The ultraviolet absorber contained in such a range of content in accordance with the use may provide a sufficient climate resistance to the thermoplastic resin.

As mentioned above, the thermoplastic polymer resins, in particular the polycarbonate resins, comprising repeating units of formulae (II), (IIa), (IIa'), (IIb), (IIc), (IId), (IIe) and (IIf), respectively, as described herein, provide high transparency and high refractive index to thermoplastic resins, which therefore are suitable for preparing optical devices, where high transparency and high refractive index is required. More precisely, the thermoplastic polycarbonates having structural units of formulae (II), (Ia), (Ia'), (IIb), (IIc), (IId), (IIe) and (IIf), respectively, are characterized by having a high refractive index, which is preferably at least 1.660, more preferably at least 1.680, in particular at least 1.690.

The contribution of the monomer of the formulae (I), (Ia), (Ia'), (Ib), (Ic), (Id), (Ie) and (If), respectively, to the refractive index of the thermoplastic resin, in particular a polycarbonate resin, will depend from the refractive index of said monomer and the relative amount of said monomer in the thermoplastic resin. In general, a higher refractive index of the monomer contained in the thermoplastic resin will result in a higher refractive index of the resulting thermoplastic resin. Apart from that, the refractive index of a thermoplastic resin comprising structural units of the formula (II) can be calculated from the refractive indices of the monomers used for preparing the thermoplastic resin, either from the refractive index of the monomers or ab initio, e.g. by using the computer software ACD/ChemSketch 2012 (Advanced Chemistry Development, Inc.).

In the following table B the calculated refractive indices for some homopolycarbonates consisting of structural units of the formulae (Ia') and (ill-1) are given:

TABLE B

| # | $R^{x1}$ | $R^{x2}$ | Ar | $n_D$ (calc.) |
|---|---|---|---|---|
| 1 | H | H | phenyl | 1.68 |
| 2 | H | H | 1-naphthyl | 1.71 |
| 3 | H | H | 2-naphthyl | 1.71 |
| 4 | H | H | 9-phenanthryl | 1.73 |
| 5 | H | H | 4-phenylphenyl | 1.68 |
| 6 | H | H | 3-phenylphenyl | 1.68 |
| 7 | H | H | 4-phenoxyphenyl | 1.68 |
| 8 | H | H | 9H-fluoren-2-yl | 1.71 |
| 9 | H | H | 1,2-dihydroacenaphthylen-5-yl | 1.73 |
| 10 | H | H | dibenzofuran-2-yl | 1.73 |
| 11 | H | H | dibenzofuran-4-yl | 1.73 |
| 12 | H | H | dibenzothienyl-2-yl | 1.74 |
| 13 | H | H | dibenzothienyl-4-yl | 1.74 |
| 14 | H | H | 4-quinolinyl | 1.72 |
| 15 | H | H | 2-quinolinyl | 1.72 |
| 16 | H | H | 3-quinolinyl | 1.72 |
| 17 | H | H | 1-isoquinolinyl | 1.72 |
| 18 | H | H | 4-isoquinolinyl | 1.72 |
| 19 | H | H | 1H-indol-3-yl | 1.70 |
| 20 | H | H | 1H-pyrrol-2-yl | 1.70 |
| 21 | H | H | 1H-pyrrol-3-yl | 1.70 |
| 22 | H | H | 2-pyridyl | 1.69 |
| 23 | H | H | 3-pyridyl | 1.69 |
| 24 | H | H | 4-pyridyl | 1.69 |
| 25 | H | H | 5-pyrimidinyl | 1.69 |
| 26 | H | H | 2-cyanophenyl | 1.76 |
| 27 | H | H | 3-cyanophenyl | 1.76 |
| 28 | H | H | 4-cyanophenyl | 1.76 |
| 29 | H | H | 4-cyano-1-naphthyl | 1.79 |
| 30 | H | H | 5-cyano-1-naphthyl | 1.79 |
| 31 | H | H | 4-cyano-2-naphthyl | 1.79 |
| 32 | H | H | 6-cyano-2-naphthyl | 1.79 |

In case of thermoplastic copolymer resins, the refractive index of the thermoplastic resin, in particular a polycarbonate resin, can be calculated from the refractive indices of the homopolymers of the respective monomers, which form the copolymer resin, by the following so called "Fox equation":

$$1/n_D = x_1/n_{D1} + x_2/n_{D2} + \ldots x_n/n_{Dn},$$

where $n_D$ is the refractive index of the copolymer, $x_1$, $x_2$, ... $x_n$ are the mass fractions of the monomers 1, 2, ... n in the copolymer and $n_{D1}$, $n_{D2}$, ... $n_{Dn}$ are the refractive indices of the homopolymers synthesized from only one of the monomers 1, 2, ... n at a time.

In case of polycarbonates, $x_1$, $x_2$, ... $x_n$ are the mass fractions of the OH monomers 1, 2, ... n, based on the total amount of OH monomer. It is apparent that a higher refractive index of a homopolymer will result in a higher refractive index of the copolymer.

The refractive indices of the thermoplastic resins can be determined directly or indirectly. For direct determination, the refractive indices no of the thermoplastic resins are measured at wavelength of 589 nm in accordance with the protocol JIS-K-7142 using an Abbe refractometer and applying a 0.1 mm film of the thermoplastic resin. In case of the refractive indices of the homopolycarbonates of the compounds of formula (I), the refractive indices can also be determined indirectly. For this, a co-polycarbonate of the respective monomer of formula (I) with 9,9-bis(4-(2-hydroxyethoxy)phenyl)-fluorene and diphenyl carbonate is prepared according to the protocol of example 1 in column 48 of U.S. Pat. No. 9,360,593 and the refractive indices no of the co-polycarbonate is measured at wavelength of 589 nm in accordance with the protocol JIS-K-7142 using an Abbe refractometer and applying a 0.1 mm film of the co-polycarbonate. From the thus measured refractive indices no, the refractive index of the homopolycarbonate of the respective monomer can be calculated by applying the Fox equation and the known refractive index of 9,9-bis(4-(2-hydroxyethoxy)phenyl)fluorene ($n_D$(589 nm)=1.639).

As mentioned before, compounds of formula (I), which do not bear color-imparting radicals, such as some of the radicals Ar, R and R', can also be obtained in a purity, which provides for a low yellowness index Y.I., as determined in accordance with ASTM E313, which may also be important for the use in the preparation of optical resins.

More precisely, the yellowness index Y.I., as determined in accordance with ASTM E313, of the compounds of formula (I) preferably does not exceed 200, more preferably 100, even more preferably 50, in particular 20 or 10.

Another aspect of the present invention relates to an optical device made of a thermoplastic resin as defined above, where the thermoplastic resin comprising a structural unit represented by the formula (II) and optionally of formula (V). As regards to the preferred meanings and preferred embodiments of the structural units of the formulae (II) and (V), reference is made to the statements given above.

An optical device made of an optical resin comprising the repeating units of the formula (II) and optionally repeating units of the formula (V) as defined herein are usually optical molded articles such as optical lenses, for example car head lamp lenses, Fresnel lenses, fθ lenses for laser printers, camera lenses, lenses for glasses and projection lenses for rear projection TV's, CD-ROM pick-up lenses, but also optical disks, optical elements for image display media, optical films, film substrates, optical filters or prisms, liquid crystal panels, optical cards, optical sheets, optical fibers, optical connectors, eposition plastic reflective mirrors, and the like. It is also useful for producing a transparent conductive substrate usable for an optical device suitable as a structural member or a functional member of a transparent conductive substrate for a liquid crystal display, an organic EL display, a solar cell and the like.

The optical lens produced from the thermoplastic resin according to the present invention has a high refractive index and a low Abbe number, and is highly moisture and heat resistant. Therefore, the optical lens can be used in the field in which a costly glass lens having a high refractive index is conventionally used, such as for a telescope, binoculars, a TV projector and the like. It is preferred that the optical lens is used in the form of an aspherical lens. Merely one aspherical lens may make the spherical aberration substantially zero. Therefore, it is not necessary to use a plurality of spherical lenses to remove the spherical aberration. Thereby the weight and the production cost of a device including the spherical aberration is decreased. An aspherical lens is useful especially as a camera lens among various types of optical lenses. The present invention easily provides an aspherical lens having a high refractive index and a low level of birefringence, which is technologically difficult to produce by processing glass.

An optical lens of the present invention may be formed, for example, by injection molding, compression molding, injection compression molding or casting the resin comprising the repeating units of the formula (II) and optionally repeating units of the formula (V) as defined herein.

The optical lens of the present invention is characterized by a small optical distortion. An optical lens comprising a conventional optical resin has a large optical distortion. Although it is not impossible to reduce the value of an optical distortion by molding conditions, the condition widths are very small, thereby making molding extremely difficult. Since the resin having repeating units of the formula (II) and optionally repeating units of the formula (V) as defined herein has an extremely small optical distortion caused by the orientation of the resin and a small molding distortion, an excellent optical element can be obtained without setting molding conditions strictly.

To manufacture the optical lens of the present invention by injection molding, it is preferred that the lens should be molded at a cylinder temperature of 260° C. to 320° C. and a mold temperature of 100° C. to 140° C.

The optical lens of the present invention is advantageously used as an aspherical lens as required. Since spherical aberration can be substantially nullified with a single aspherical lens, spherical aberration does not need to be removed with a combination of spherical lenses, thereby making it possible to reduce the weight and the production cost. Therefore, out of optical lenses, the aspherical lens is particularly useful as a camera lens.

Since resins having repeating units of the formula (II) and optionally repeating units of the formula (V) as defined herein have a high moldability, they are particularly useful as the material of an optical lens which is thin and small in size and has a complex shape. As a lens size, the thickness of the center part of the lens is 0.05 to 3.0 mm, preferably 0.05 to 2.0 mm, more preferably 0.1 to 2.0 mm. The diameter of the lens is 1.0 to 20.0 mm, preferably 1.0 to 10.0 mm, more preferably 3.0 to 10.0 mm. It is preferably a meniscus lens which is convex on one side and concave on the other side.

The surface of the optical lens of the present invention may have a coating layer such as an antireflection layer or a hard coat layer as required. The antireflection layer may be a single layer or a multi-layer and composed of an organic material or inorganic material but preferably an inorganic material. Examples of the inorganic material include oxides and fluorides such as silicon oxide, aluminum oxide, zirconium oxide, titanium oxide, cerium oxide, magnesium oxide and magnesium fluoride.

The optical lens of the present invention may be formed by an arbitrary method such as metal molding, cutting, polishing, laser machining, discharge machining or edging. Metal molding is preferred.

An optical film produced by the use of the thermoplastic resin according to the present invention is high in transparency and heat resistance, and therefore is preferably usable for a liquid crystal substrate film, an optical memory card or the like. In order to avoid foreign objects from being incorporated into the optical film as much as possible, the molding needs to be performed in a low dust environment, needless to say. The dust environment is preferably of class 6 or lower, and more preferably of class 5 or lower.

The following examples serve as further illustration of the invention.

I. Abbreviations

DCM: dichloromethane
MEK: 2-butanone
MeOH: methanol
EtOH: ethanol
MTBE: methyl tert-butyl ether
RT: room temperature
THF: tetrahydrofurane
TLC: thin layer chromatography
BPEF: 9,9-bis(4-(2-hydroxyethoxy)phenyl)fluorene
BNE: 2,2'-bis(2-hydroxyethoxy)-1,1'-binaphthalene
DPC: Diphenyl carbonate

II. Preparation of the Compounds of Formula (I)

II.1 Analytics $^1$H-NMR spectra were determined at 23° C. using a 400 MHz NMR-spectrometer Avance III 400 HD from Bruker BioSpin GmbH. If not stated otherwise the solvent was $CDCl_3$ IR spectra were recorded by ATR FT-IR, using a Shimadzu FTIR-8400S spectrometer (45 no. of scans, resolution 4 $cm^{-1}$; apodization: Happ-Genzel).

Melting points of the compounds were determined by Buchi Melting Point B-545.

UPLC (Ultra Performance Liquid Chromatography) analyses were carried out using the following system and conditions:

Waters Acquity UPLC H-Class Systems; column: Acquity UPLC BEH C18, 1.7 µm, 2×100 mm; column temperature: 40° C., gradient: acetonitrile/water: with acetonitrile at 0 min 50%, at 4 min 100%; at 5.8 min 100%; at 6.0 min 50%; at 8.0 min 50%); injection volume: 0.4 µl; run time: 8 min; detection at 210 nm.

The yellowness index YI of the compounds of formula (I) can be determined by analogy to ASTN E313 using the following protocol: 1 g of the compound of formula (I) is dissolved in 19 g of a mixture of MEK/water 95:5 (v/v). The solution is transferred into a 50 mm cuvette and transmission is determined in the range 300-800 nm by a Shimadzu UV-Visible spectrophotometer UV-1650PC. A mixture of MEK/water 95:5 (v/v) is used as a reference. From the spectra the yellowness index can be calculated by using the Software "RCA-software UV2DAT" in accordance with ASTM E308 (Standard practice for computing the colors of objects by using the CIE System) und ASTM E 313 (Standard practice for calculating yellowness and whiteness indices from instrumentally measured color coordinates).

The haze can be determined by measuring the transmission at 860 nm of a 5% solution of the respective compound of formula (I) in a mixture of MEK/water 95:5 (v/v) by a standard nephelometer.

II.2 Preparation Examples

Example 1: Preparation of 2-[[1-[[2-(2-hydroxyethoxy)-1-naphthyl]-phenyl-methyl]-2-naphthyl]oxy]ethanol, (compound of formula (Ia'.1)

1.1: 1-[[2-Hydroxy-1-naphthyl]-phenyl-methyl]-2-hydroxy-naphthalene (compound of formula (VI) with $R^1$ and $R^2$ being hydrogen, Ar being phenyl and $X^1$, $X^2$, $X^3$ and $X^4$ being CH)

288.34 g (2 mol) of 2-naphthol were dissolved in 600 g (ca. 763 mL) of isopropanol at RT. To this homogeneous solution 111.43 g (ca. 106.1 mL, 1.05 mol) of benzaldehyde and 19.22 g (12.987 mL, 200 mmol) of methanesulfonic acid were added at RT. The initially homogeneous reaction mixture was stirred for at least 1.5 days at RT until a thick slurry was formed. The reaction was controlled via TLC (mobile phase: MeOH/water 7:3 (v/v)). Precipitated solid was filtered off, washed subsequently with 40 g of isopropanol, and then with 50 g of pentane and the solid was dried in vacuo at max. 30° C. under reduced pressure (180 mbar). The first crop of the desired product was 161.69 g (ca. 43%). The mother liquor was concentrated using a rotary evaporator (at max. 40° C.) and stirred several hours at RT until a thick slurry was again formed. The precipitated solid was filtered off, washed with 20 g of isopropanol, then with 25 g of pentane, and was finally dried in vacuo at max. 30° C. and 5 mbar. The second crop of the desired product was 143.76 g (ca. 38.2%). Finally using the same procedure described above, additionally ca. 57.36 g (ca. 15.2%) as a third crop of the title compound was isolated, affording the title compound in a total yield of 362.81 g (ca. 96.38%) as white crystalline powder, which was subjected to the next step without additional purification.

m.p.=209-210° C.

1.2: 2-[[1-[[2-(2-hydroxyethoxy)-1-naphthyl]-phenyl-methyl]-2-naphthyl]oxy]ethanol (compound of formula (Ia'.1)

A 1 L-three-neck round-bottom flask with reflux-condenser was purged with argon or nitrogen and charged with 50 g (132.82 mmol) of 1-[[2-hydroxy-1-naphthyl]-phenyl-methyl]-2-hydroxy-naphthalene, which was then suspended in 270 mL (ca. 234 g) of toluene. Afterwards 35.1 g (398.5 mmol) of ethylene carbonate and 5.51 g (39.87 mmol) of potassium carbonate were added to the suspension and the reaction mixture was stirred for 6-10 hours under reflux. The reaction was controlled via TLC (mobile phase: MeOH/water 7:3 (v/v)). After TLC analysis indicated completion of the conversion, the reaction mixture was cooled to 70° C., and 65 mL water were then slowly added to the mixture. Following completion of the gas evolution and phase separation, the organic phase was washed twice with 65 mL of 10% aqueous solution of sodium hydroxide, each, and twice or more with water until the aqueous wash solution is neutral (pH 7). The organic phase was then concentrated with a rotary evaporator until an almost oily product was formed, 400-500 g of MTBE were added and the crude product allowed to crystallize at RT. The obtained crystalline solid was filtered off, washed with MTBE and dried to afford 29.4 g of the title compound (yield: 47.7%). After concentration of the mother liquor additionally 15.54 g (ca. 25.2%) of the title compound were isolated. Total yield of the crude 2,2'-[(phenylmethylene)bis(1,2-naphthyleneoxy)]diethanol was 44.94 g (ca. 72.8%). 43.8 g of the crude product were dissolved in 650 g of THF and the obtained homogeneous solution was treated with 4.5 g of activated charcoal at 50° C., filtered through Celite® and the solvent was completely removed with a rotary evaporator. Finally the title compound was purified by crystallization from MTBE to give 42.99 g of the pure title compound as colorless crystals with chemical purity of 97.8%. After recrystallization of the title compound from MEK a chemical purity of >99% (UPLC) was achieved.

m.p.: 162.8-163.8° C.;
$^1$H NMR (400 MHz, CDCl$_3$): δ=2.51 (br s, 2H), 3.28 (ddd, J=12.54, 5.92, 2.66 Hz, 2H), 3.31 (ddd, J=12.54, 5.92, 2.66 Hz, 2H), 3.68 (ddd, J=9.78, 5.87, 2.57 Hz, 2H), 3.78 (ddd, J=9.78, 5.87, 2.57 Hz, 2H), 7.04 (s, 1H), 7.35-7.58 (m, 12H), 7.93-8.10 (m, 5H) ppm;

IR [cm$^{-1}$]: 817.85 (71.0); 850.64 (78.7); 879.57 (72.8); 904.64 (76.4); 960.58 (76.8); 976.01 (81.1); 1031.95 (65.4); 1047.38 (62.0); 1062.81 (58.5); 1095.6 (60.6); 1145.75 (75.7); 1186.26 (82.3); 1215.19 (65.8); 1240.27 (62.1); 1261.49 (58.6); 1300.07 (82.7); 1317.43 (76.8); 1344.43 (81.5); 1369.5 (81.5); 1396.51 (86.9); 1411.94 (83.5); 1429.3 (77.3); 1450.52 (76.8); 1465.95 (77.6); 1491.02 (78.8); 1510.31 (69.7); 1597.11 (70.9); 1622.19 (78.5); 2868.24 (86.5); 2916.47 (87.9); 2928.04 (87.4); 3182.65 (87.9); 3282.95 (86.0); 3360.11 (86.5); 3458.48 (87.4) cm$^{-1}$.

Example 2: Preparation of 2-[[1-[[2-(2-hydroxyethoxy)-1-naphthyl]-(1-naphthyl)methyl]-2-naphthyl]oxy]ethanol (compound of formula (Ia'.2)

2.1: 1-[[2-Hydroxy-1-naphthyl]-(1-naphthyl)methyl]-2-hydroxy-naphthalene (compound of formula (VI) with R$^1$ and R$^2$ being hydrogen, Ar being 1-naphthyl and X$^1$, X$^2$, X$^3$ and X$^4$ being CH)

57.67 g (400 mmol) of 2-naphthol were dissolved in 560 mL (ca. 744.8 g) of DCM and then 35.35 g (215 mmol) of 1-naphthaldehyde and 3.84 g (40 mmol, 10 mol-%) of methanesulfonic acid were added at RT. The reaction mixture was stirred at RT until TLC analysis (mobile phase: MeOH/water 8:2 (v/v)) indicated complete consumption of 2-naphthol. The reaction mixture was quenched by neutralization with saturated aqueous solution of sodium carbonate (50-60 mL). After phase separation the organic phase was washed with water (2×100 mL) and the collected aqueous extracts were extracted with DCM (3×50 mL). Finally, DCM is completely evaporated from the collected organic phases using a rotary evaporator and the crude product was taken up in TBME (350 mL). The obtained suspension was stirred for 1 hour at RT. Finally, the solid was filtered off, washed with TBME (3×20 g) and dried, yielding 80.7 g (ca. 94.6%) of the title compound as an off-white crystalline solid with a chemical purity of 99.26% (UPLC).

m.p.: 201.6° C.

2.2: 2-[[1-[[2-(2-Hydroxyethoxy)-1-naphthyl]-(1-naphthyl)methyl]-2-naphthyl]oxy]ethanol (compound of formula (Ia'.2)

A 2 L-three-neck round-bottom flask with reflux-condenser was purged with argon or nitrogen and charged with 200.46 g (470 mmol) of 1-[[2-Hydroxy-1-naphthyl]-(1-naphthyl)methyl]-2-hydroxy-naphthalene, which was then suspended in 940 mL (ca. 815 g) of toluene. Afterwards 124.17 g (1.41 mol) of ethylene carbonate and 19.5 g (141 mmol) of potassium carbonate were added to the suspension and the reaction mixture was stirred for 6-10 hours under reflux. The reaction was controlled via TLC (mobile phase: MeOH/water 8:2 (v/v)). During the reaction a solid precipitated. After TLC analysis indicated complete conversion, the reaction mixture was cooled to 70° C. and 65 mL of water were then slowly added to the mixture. After completion of the gas evolution the solid was filtered off, washed with toluene (2×100 mL) and with water (3×100 mL). The solid was the suspended in MEK and water was removed via distillation of a MEK/water azeotrope. Finally, the product was filtered off, washed with MEK to obtain 124.68 g (ca. 55.2%) of the title compound as a white solid. After purification via slurry wash in MEK at 60° C., filtration and drying the title compound was obtained in a yield of 118.15 g (ca. 52.3%) and a chemical purity of 96.48% (UPLC).

m.p.: 259.4-259.8° C.;

$^1$H NMR (400 MHz, DMSO-d$_6$): δ=2.77-3.19 (m, 4H), 3.24-3.80 (m, 4H), 4.31 (br s, 1H), 4.50 (br s, 1H), 6.98 (s, 1H), 7.16-8.16 (m, 19H) ppm;

IR [cm$^{-1}$]: 812.06 (51.0); 856.42 (69.5); 893.07 (73.7); 929.72 (85.9); 958.65 (77.2); 1010.73 (76.8); 1026.16 (63.2); 1041.6 (61.9); 1060.88 (58.2); 1072.46 (58.9); 1091.75 (70.2); 1143.83 (74.3); 1186.26 (83.5); 1234.48 (62.4); 1259.56 (61.3); 1269.2 (59.1); 1336.71 (75.2); 1373.36 (79.4); 1394.58 (80.2); 1429.3 (78.3); 1448.59 (76.5); 1469.81 (82.3); 1506.46 (70.0); 1597.11 (68.6); 1620.26 (76.6); 2868.24 (87.7); 2935.76 (85.9); 3049.56 (87.8); 3360.11 (84.3) cm$^{-1}$.

Example 3: Preparation of 2-[[1-[[2-(2-hydroxyethoxy)-1-naphthyl]-(2-naphthyl)methyl]-2-naphthyl]oxy]ethanol (compound of formula (Ia'.3)

3.1: 1-[[2-Hydroxy-1-naphthyl]-(2-naphthyl)methyl]-2-hydroxy-naphthalene (compound of formula (VI) with R$^1$ and R$^2$ being hydrogen, Ar being 2-naphthyl and X$^1$, X$^2$, X$^3$ and X$^4$ being CH)

72.085 g (500 mmol) of 2-naphthol were dissolved in 150 g (ca. 191 mL) of isopropanol at RT. To this homogeneous solution 40,639 g (255 mol) of 2-naphthaldehyde and 4.81 g (50 mmol) of methanesulfonic acid were added at RT. The initially homogeneous reaction mixture was stirred for 24 hours at RT until a thick slurry was formed. The reaction was controlled via TLC (mobile phase: MeOH/water 2:1 (v/v)). Precipitated solid was filtered off, washed subsequently with isopropanol (3×20 mL) and pentane (2×50 mL) and the solid was then dried in vacuo at max. 30° C. and 5 mbar. The thus obtained first crop of the desired product was 27.0 g (ca. 25.3%) with a chemical purity of >96% (UPLC). The mother liquor was concentrated using a rotary evaporator (at max. 40° C.) and then stirred several hours at RT until a thick slurry was again formed. The precipitated solid was filtered off, washed with 20 g of isopropanol, then with 25 g of pentane, and was finally dried in vacuo at max. 30° C. and 180 mbar. The thus obtained second crop of the title compound was 70.0 g (ca. 65.6%) with purity of >92% (UPLC). The title compound was obtained as white crystalline powder in a total yield of ca. 97.0 g (ca. 90.9%) and subjected for the next step without further purification.

m.p.: 177-179° C.

3.2: 2-[[1-[[2-(2-Hydroxyethoxy)-1-naphthyl]-(2-naphthyl)methyl]-2-naphthyl]oxy]ethanol (compound of formula (Ia'.3)

A 2 L-three-neck round-bottom flask with reflux-condenser was purged with argon or nitrogen and charged with 127.95 g (300 mmol) of 1-[[2-hydroxy-1-naphthyl]-(2-naphthyl)methyl]-2-hydroxy-naphthalene, which was then suspended in 600 mL (ca. 520 g) of toluene. Afterwards 79.3 g (900 mmol) of ethylene carbonate and 12.11 g (90 mmol) of potassium carbonate were added to the suspension and the reaction mixture was stirred for 6-10 hours under reflux. The reaction was controlled via TLC (mobile phase: MeOH/water 7:3 (v/v)). During the reaction a solid precipitated. After TLC analysis indicated complete conversion, the reaction mixture was cooled to 70° C. and 170 mL water were then slowly added to the mixture. After completion of the gas evolution and phase separation, the organic phase was washed twice with 170 mL of a 10% aqueous solution of sodium hydroxide, each, and then twice or more with water until the aqueous wash solution is neutral (pH 7). The organic phase was then concentrated with a rotary evaporator and the crude product was crystallized from toluene at 50° C. The obtained crystalline solid was filtered off, washed with cold toluene, then with pentane and dried to afford 101.64 g (ca. 65.84%) of the title compound. After concentration of the mother liquor additionally 11.94 g (ca. 7.73%) of the title compound were isolated. Total yield of the crude title compound was 113.58 g (ca. 73.57%). After purification with activated charcoal at 50° C., filtration through Celite® and recrystallization from MEK or toluene, the title compound with a purity of 99.76% (UPLC) was obtained.

m.p.=164° C.;

$^1$H NMR (400 MHz, CDCl$_3$): δ=2.28 (br s, 2H), 2.93-3.03 (m, 1H), 3.10-3.26 (m, 3H), 3.47-3.55 (m, 1H), 3.65-3.79 (m, 3H), 7.15-7.44 (m, 10H), 7.558 (s, 1H), 7.60-7.91 (m, 9H) ppm;

IR [cm$^{-1}$]: 804.34 (50.8); 856.42 (64.0); 900.79 (70.2); 960.58 (77.3); 1030.02 (61.8); 1062.81 (54.9); 1093.67 (66.8); 1124.54 (85.9); 1149.61 (76.0); 1163.11 (81.0); 1207.48 (68.0); 1238.34 (62.8); 1259.56 (56.8); 1292.35 (82.8); 1334.78 (75.9); 1352.14 (83.5); 1371.43 (79.3); 1410.01 (83.1); 1429.3 (77.4); 1448.59 (76.0); 1469.81 (78.4); 1510.31 (69.9); 1573.97 (87.5); 1597.11 (70.1); 1620.26 (76.4); 2872.1 (85.8); 2935.76 (84.9); 3053.42 (87.0); 3383.26 (84.8); 3419.9 (85.0); 3564.57 (86.5) cm$^{-1}$.

III. Preparation of the Resins

III.1 Analytics

III.1.1 Measurement Method of Weight Average Molecular Weight (Mw) and Number Average Molecular Weight (Mn)

The weight average molecular weight (Mw) was measured using the HLC-8320GPC device from Tosoh Corporation as a GPC device, the TSKguardcolumn SuperMPHZ-Mone as a guard column, and three TSKgel SuperMultiporeHZ-M(s) connected in series as analysis columns. The measurement conditions were as follows.

Solvent: HPLC grade chloroform
Injection Volume: 10 μL
Concentration of Sample: 0.2 w/v % HPLC grade chloroform solution
Solvent flow velocity": 0.35 ml/min
Measurement Temperature: 40° C.
Detecting Device: RI The polystyrene converted weight average molecular weights (Mw) and number average molecular weights (Mn) are calculated using the previously prepared standard curve of polystyrene. Specifically, the standard curve was prepared using a standard polystyrene of which the molecular weight was known ("PStQuick MP-M" from Tosoh Corporation which has molecular weight distribution value of 1). Further, a calibration curve was obtained by plotting the elution time and molecular weight value of each of the peaks based on the measured data of the standard polystyrene, and conducting three-dimensional approximation. The values for Mw and Mn are calculated based on the following calculation formulae.

$$Mw=\Sigma(Wi \times Mi)+\Sigma(Wi)$$

$$Mn=\Sigma(Ni \times Mi)+\Sigma(Wi)$$

In the calculation formula, "i" represents the "i"th dividing point, "Wi" represents the molecular weight (g) of the polymer at the "i"th dividing point, "Ni" represents the number of the molecules of the polymer at the "i"th dividing point, and "Mi" represents the molecular mass at the "i"th dividing point. The molecular mass (M) represents the value of the molecular mass of polystyrene at the corresponding elution time in the calibration curve.

III.1.2 Refractive Index ($n_D$)

The refractive index of a film having a thickness of 0.1 mm formed of a polycarbonate resin produced in an example was measured by use of an Abbe refractive index meter by a method of JIS-K-7142 at a wavelength of 589 nm.

III.1.3 Abbe Number (v)

The refractive index of a film having a thickness of 0.1 mm formed of a polycarbonate resin produced in an example was measured by use of an Abbe refractive index meter at 23° C. at wavelengths of 486 nm, 589 nm and 656 nm. Then, the Abbe number was calculated by use of the following equation:

$$v=(n_D-1)/(n_F-n_C)$$

$n_D$: refractive index at a wavelength of 589 nm
$n_C$: refractive index at a wavelength of 656 nm
$n_F$: refractive index at a wavelength of 486 nm

III.1.4 Glass Transition Temperature (Tg)

The glass transition temperature was measured by differential scanning calorimetry (DSC) according to JIS K 7121-1987. The measuring device was a X-DSC7000 from Hitachi High-Technologies.

III.1.5 Measurement of b Value

The respective resin was dried at 120° C. for 4 hours in vacuum, and then injection-molded by an injection molding device (FANUC ROBOSHOT α-S30iA) at a cylinder temperature of 270° C. and a mold temperature of Tg−10° C. to obtain a disc-shaped test plate piece having a diameter of 50 mm and a thickness of 3 mm. This test plate piece was used to measure the b value by a method according to JIS-K7105. When the b value is smaller, the plate is less yellowish and thus the hue is better. For the measurement, a spectral color difference meter type SE2000 of Nippon Denshoku Industries Co., Ltd. was used.

III.1.6 Total Light Transmittance (TLT)

A plate having a thickness of 3 mm was produced from the respective polycarbonate resin by the protocol described in section III.1.5 for the measurement of the b value. The total light transmittance of measured by use of SE2000 spectral color difference meter produced by Nippon Denshoku Industries Co., Ltd. by a method of JIS-K-7361-1.

The total light transmittance of these plates were measured before a PCT treatment and thereafter. The latter value is given in table C in column TLT-PCT.

III.1.7 Amount of Vinyl Terminal Group

The amount of vinyl terminal groups was determined by $^1$H-NMR measurement under the following conditions.
Device: AVANZE III HD 500 MHz produced by Bruker
Flip angle: 30 degrees
Wait time: 1 second
Accumulate number of times: 500 times
Measurement temperature: room temperature (298K)
Concentration: 5 wt %
Solvent: Deuterated chloroform
Inner standard substance: tetramethylsilane (TMS) 0.05 wt %

III.1.8 Determination of Impurities in the Resin

Concentrations of phenol, diphenylcarbonate (DPC) and monomer in the polycarbonate resin was measured according to the following protocol.

0.5 g of the resin sample was dissolved in 50 ml of tetrahydrofuran to obtain a resin solution. A calibration curve was created from a pure form of each of compounds as a preparation. 2 µL of sample solution was quantitatively analyzed by LC-MS under the following measurement conditions. The detection limit under the measurement conditions is 0.01 ppm.

Measurement device (LC part): Agilent Infinity 1260 LC System
Column: ZORBAX Eclipse XDB-18 and guard cartridge
Mobile phase:
  Eluent A: 0.01 mol/L—aqueous solution of ammonium acetate
  Eluent B: 0.01 mol/L—methanol solution of ammonium acetate
  Eluent C: THF
Gradient program of the mobile phase:
As shown in Table 1, different mixtures of eluents A through C were used as mobile phases. The mobile phases were caused to flow in the column for 30 minutes while the compositions of the mobile phases were switched when the time (minutes) shown in Table 1 lapsed.

TABLE 1

| Time | Mobile Phase Composition (% by Volume) | | |
|---|---|---|---|
| (min.) | A | B | C |
| 0 | 10 | 75 | 15 |
| 10.0 | 9 | 67.5 | 23.5 |
| 10.1 | 0 | 25 | 75 |
| 30.0 | 0 | 25 | 75 |

Flow rate: 0.3 ml/min.
Column temperature: 45° C.
Detector: UV (225 nm)
Measurement device (MS part): Agilent 6120 single quad LCMS System
Ionization source: ESI
Polarity: Positive (DPC) and negative (PhOH)
Fragmentor: 70 V
Dry gas: 10 L/min., 350° C.
Nebulizer: 50 psi
Capillary voltage: 3000 V (positive), 2500 V (negative)
Ion measured

TABLE 2

| Monomer | Ion Type | m/z |
|---|---|---|
| PhOH | [M − H]$^-$ | 93.1 |
| DPC | [M + NH$_4$]$^+$ | 232.1 |

Amount of injected sample: 2 µL

III.1.9 Moldability of Resins

The moldability of the polycarbonate resins was evaluated preparing plates as described in protocol 3.1.5 and visually assessing the quality of the plates according to the following grades A to D:

A: Molded piece had no void space and no wave was found on the surface of the molded piece.
B: Molded piece had void space while no wave was found on the surface of the molded piece.
C: Molded piece had no void space while waves were found on the surface of the molded piece.
D: Molded piece had void space while waves were found on the surface of the molded piece.

III.2 Preparation Examples

Example 4-1

7.70 g (0.016 mol) of 2-[[1-[[2-(2-hydroxyethoxy)-1-naphthyl]-phenyl-methyl]-2-naphthyl]oxy]ethanol (compound of the formula (Ia'.1)), 28.19 g (0.064 mol) of BPEF, 17.73 g (0.083 mol) of DPC and 32 μl ($8.0 \times 10^{-7}$ mol) of a $2.5 \times 10^{-2}$ mol/L aqueous solution of sodium hydrogen carbonate were put into a 300 ml four-neck flask reactor in a nitrogen atmosphere. The mixture was heated to 190° C. to start the reaction. The reaction mixture was stirred at 190° C. for 60 minutes and then heated to 200° C. The reaction conditions were maintained for further 20 minutes. Then, the pressure was adjusted to 200 mmHg, and the reaction conditions were maintained for further 20 minutes. At this point, phenol generated as a byproduct started to distill off. Then, the reaction mixture was heated to 230° C. and the reaction conditions were maintained for further 10 minutes. Then, the pressure was adjusted to 150 mmHg and the reaction conditions were maintained for further 10 minutes. The reaction mixture was heated to 240° C. while the pressure was adjusted to lower than or equal to 1 mmHg. The reaction mixture was stirred for 30 minutes with maintaining the temperature and pressure. After the reaction was completed, pressure equalization was achieved by introducing nitrogen into the reactor and the generated polycarbonate was removed from the reactor and analyzed. The results are summarized in table C.

In the polycarbonate obtained in Example 4-1, the content of phenol was 300 ppm while the content of diphenylcarbonate was 150 ppm.

Example 4-2

Substantially the same operation was performed as in example 4-1 except that 19.20 g (0.0414 mol) of the compound of formula (Ia'.1) and 17.60 g (0.040 mol) of BPEF were used as dihydroxy compounds to obtain a polycarbonate resin.

Example 4-3

Substantially the same operation was performed as in example 4-1 except that 8.30 g (0.0161 mol) of 2-[[1-[[2-(2-hydroxyethoxy)-1-naphthyl]-(1-naphthyl)methyl]-2-naphthyl]oxy]ethanol (compound of formula (Ia'.2)) and 28.30 g (0.0645 mol) of BPEF were used as dihydroxy compounds to obtain a polycarbonate resin.

Example 4-4

Substantially the same operation was performed as in example 4-1 except that 21.30 g (0.0414 mol) of the compound of formula (Ia'.2) and 18.10 g (0.0413 mol) of BPEF were used as dihydroxy compounds to obtain a polycarbonate resin.

Example 4-5

Substantially the same operation was performed as in example 4-1 except that 8.30 g (0.0161 mol) of 2-[[1-[[2-(2-hydroxyethoxy)-1-naphthyl]-(2-naphthyl)methyl]-2-naphthyl]oxy]ethanol (compound of formula (Ia'.3)) and 28.30 g (0.0645 mol) of BPEF were used as dihydroxy compounds to obtain a polycarbonate resin.

Example 4-6

Substantially the same operation was performed as in example 4-1 except that 21.30 g (0.0414 mol) of the compound of formula (Ia'.3) and 18.10 g (0.0413 mol) of BPEF were used as dihydroxy compounds to obtain a polycarbonate resin.

Reference Example 5

Substantially the same operation was performed as in example 4-1 except that 6.20 g (0.0166 mol) of BNE and 29.00 g (0.0661 mol) of BPEF were used as dihydroxy compounds to obtain a polycarbonate resin.

Properties of the resins obtained in Examples 4-1 to 4-6 and Reference Example 5 are shown in Table C.

TABLE C

| | Molar Ratio of Dihydroxy Compounds | | | | | Molecular Weight | | |
|---|---|---|---|---|---|---|---|---|
| Example | Compound (Ia'.1) | Compound (Ia'.2) | Compound (Ia'.3) | BPEF | BNE | $M_W$ | Mn | Mw/Mn |
| 4-1 | 20.0 | 0.0 | 0.0 | 80.0 | 0.0 | 68976 | 7751 | 8.899 |
| 4-2 | 50.8 | 0.0 | 0.0 | 49.2 | 0.0 | 51361 | 6928 | 7.414 |
| 4-3 | 0.0 | 20.0 | 0.0 | 80.0 | 0.0 | 16557 | 4452 | 3.719 |
| 4-4 | 0.0 | 50.1 | 0.0 | 49.9 | 0.0 | 12760 | 3780 | 3.376 |
| 4-5 | 0.0 | 0.0 | 20.0 | 80.0 | 0.0 | 50427 | 7655 | 6.587 |
| 4-6 | 0.0 | 0.0 | 50.0 | 50.0 | 0.0 | 28329 | 11997 | 2.361 |
| 5[1] | 0.0 | 0.0 | 0.0 | 80.0 | 20.0 | 69076 | 6734 | 10.258 |

| Ex. | Tg [° C.] | $n_D$ | $n_C$ | $n_F$ | Abbe no. (v) | TLT[2] [%] | b value | Moldability | TLT-PCT[3] [%] |
|---|---|---|---|---|---|---|---|---|---|
| 4-1 | 146.9 | 1.6439 | 1.6359 | 1.6644 | 22.60 | 89 | 4.0 | A | 89 |
| 4-2 | 149.8 | 1.6505 | 1.6447 | 1.6751 | 21.38 | 88 | 4.1 | B | 88 |
| 4-3 | 152.9 | 1.6498 | 1.6415 | 1.6711 | 21.97 | 89 | 4.0 | A | 89 |
| 4-4 | 165.8 | 1.6643 | 1.6469 | 1.6799 | 20.14 | 88 | 4.0 | B | 88 |

TABLE C-continued

| 4-5 | 150.9 | 1.6482 | 1.6399 | 1.6694 | 22.02 | 89 | 4.0 | A | 89 |
|---|---|---|---|---|---|---|---|---|---|
| 4-6 | 160.0 | 1.6603 | 1.6543 | 1.6869 | 20.25 | 88 | 4.0 | B | 88 |
| 5[1)] | 139.4 | 1.6446 | 1.6344 | 1.6630 | 22.53 | 85 | 4.3 | D | 85 |

[1)] reference example 5;
[2)] total light transmittance of the finished resin;
[3)] total light transmittance of the resin after PCT test.

We claim:

1. A thermoplastic resin comprising a structural unit represented by formula (II) below

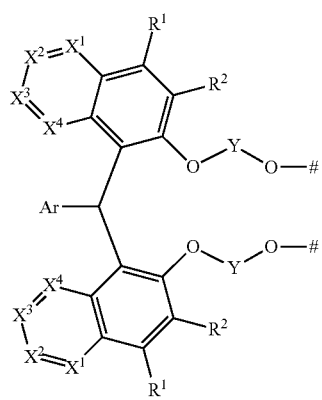 (II)

where

\# represents a connection point to a neighboring structural unit;

$R^1$, $R^2$ are hydrogen, a radical $R^a$ or $R^1$ and $R^2$ together with the carbon atoms to which they are bound may also form a fused benzene ring, which is unsubstituted or substituted by one radical $R^a$, Y represents an alkylene group having 2, 3 or 4 carbon atoms, Ar is selected from the group consisting of mono- or polycyclic aryl having from 6 to 26 carbon atoms and mono- or polycyclic hetaryl having a total of 5 to 26 atoms, which are ring members, where 1, 2, 3 or 4 of these atoms are selected from nitrogen, sulphur and oxygen, while the remainder of these atoms are carbon atoms, where mono- or polycyclic aryl and mono- or polycyclic hetaryl are unsubstituted or carry one, two, three or four radicals $R^{Ar}$;

$X^1$, $X^2$, $X^3$, $X^4$ are CH, C—$R^x$ or N, provided that in each ring at most two of $X^1$, $X^2$, $X^3$, $X^4$ are N;

$R^a$ is selected from the group consisting of fluorine, cyclopropyl, cyclobutyl, CN, R, OR, $CH_nR_{3-n}$, $NR_2$, C(O)R, C(O)$NH_2$, CH=$CH_2$, CH=CHR', $CH_2$—CH=$CH_2$, $CH_2$—CH=CHR', $CH_2$—C≡CH and $CH_2$—C≡CR';

$R^{Ar}$ is selected from the group consisting of fluorine, cyclopropyl, cyclobutyl, CN, R, OR, $CH_nR_{3-n}$, $NR_2$, C(O)R, C(O)$NH_2$, CH=$CH_2$, CH=CHR', $CH_2$—CH=$CH_2$, $CH_2$—CH=CHR', $CH_2$—C≡CH and $CH_2$—C≡CR', wherein each $R^{Ar}$ is identical or different if more than one $R^{Ar}$ is present on each ring;

$R^x$ is selected from the group consisting of halogen, cyclopropyl, cyclobutyl, CN, R, OR, $CH_nR_{3-n}$, $NR_2$, C(O)R, CH=$CH_2$, CH=CHR', $CH_2$—CH=$CH_2$, $CH_2$—CH=CHR', $CH_2$—C≡CH and $CH_2$—C≡CR', wherein each $R^x$ is identical or different if more than one $R^x$ is present on each ring;

R is selected from methyl, mono- or polycyclic aryl having from 6 to 26 carbon atoms and mono- or polycyclic hetaryl having a total of 5 to 26 atoms, which are ring members, where 1, 2, 3 or 4 of the ring atoms of hetaryl are selected from nitrogen and oxygen, while the remainder of these atoms are carbon atoms, where mono- or polycyclic aryl are unsubstituted or substituted by one, two, three or four identical or different radicals R";

R' is selected from methyl, mono- or polycyclic aryl having from 6 to 26 carbon atoms and mono- or polycyclic hetaryl having a total of 5 to 26 atoms, which are ring members, where 1, 2, 3 or 4 of the ring atoms of hetaryl are selected from nitrogen and oxygen, while the remainder of these atoms are carbon atoms, where mono- or polycyclic aryl are unsubstituted or substituted by one, two, three or four identical or different radicals R";

R" is selected from fluorine, cyclopropyl, cyclobutyl, phenyl, CN, $OCH_3$, $CH_3$, $N(CH_3)_2$, $C(O)CH_3$, CH=$CH_2$, CH=$CHCH_3$, $CH_2$—CH=$CH_2$, $CH_2$—CH=CH—$CH_3$, $CH_2$—C≡CH and $CH_2$—C≡C—$CH_3$; and n is each 0, 1, 2 or 3;

wherein the thermoplastic resin has a refractive index at 23° C. at a wavelength of 589 nm of 1.6439 or higher.

2. The thermoplastic resin of claim 1, where the structural unit is connected to one of the structures represented by formulae (III-1) to (III-5) below,

 (III-1)

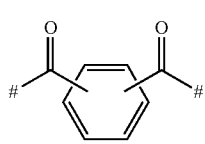 (III-2)

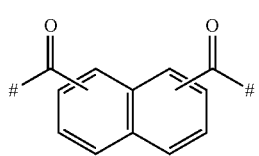 (III-3)

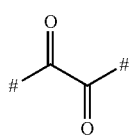 (III-4)

-continued

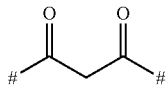
(III-5)

where # represents a connection point to a neighboring structural unit.

3. The thermoplastic resin of claim 1, which is selected from copolycarbonate resins, copolyestercarbonate resins and copolyester resins, where the thermoplastic resin in addition to structural units represented by formula (II) comprises a structural unit of the formula (V),

—O—R$^z$-A$^3$-R$^z$—O—#- (V)

where represents a connection point to a neighboring structural unit;

A$^3$ is a polycyclic radical bearing at least two benzene rings, wherein the benzene rings may be connected by A' and/or directly fused to each other and/or fused by a non-benzene carbocycle, where A$^3$ is unsubstituted or substituted by one, two or three radicals R$^{aa}$, which are selected from the group consisting of halogen, $C_1$-$C_6$-alkyl, $C_5$-$C_6$-cycloalkyl and phenyl;

A' is selected from the group consisting of a single bond, O, C=O, S, SO$_2$, CH$_2$, CH—Ar", CHAr"$_2$, CH(CH$_3$), C(CH$_3$)$_2$ and a radical of the formula (A")

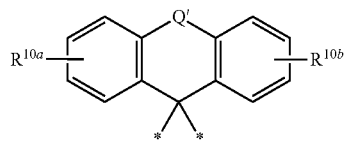
(A")

where

Q' represents a single bond, O, NH, C=O, CH$_2$ or CH=CH; and

R$^{10a}$, R$^{10b}$ independently of each other are selected from the group consisting of hydrogen, fluorine, CN, R, OR, CH$_k$R$_{3-k}$, NR$_2$, C(O)R and C(O)NH$_2$, where k is 0, 1, 2 or 3;

Ar" is selected from the group consisting of mono- or polycyclic aryl having from 6 to 26 carbon atoms and mono- or polycyclic hetaryl having a total of 5 to 26 atoms, which are ring members, where 1, 2, 3 or 4 of these atoms are selected from nitrogen, sulphur and oxygen, while the remainder of these atoms are carbon atoms, where Ar" is unsubstituted or substituted by one, two or three radicals R$^{ab}$, which are selected from the group consisting of halogen, phenyl and $C_1$-$C_4$-alkyl;

R$^z$ is a single bond, Alk$^1$ or O-Alk$^2$- where O is bound to A$^3$, and where Alk$^1$ is $C_2$-$C_4$-alkandiyl; and Alk$^2$ is $C_2$-$C_4$-alkandiyl.

4. The thermoplastic resin of claim 3, where the structural unit of the formula V is represented by one of the following formulae V-1 to V-8:

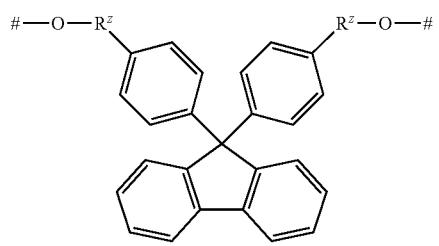
V-1

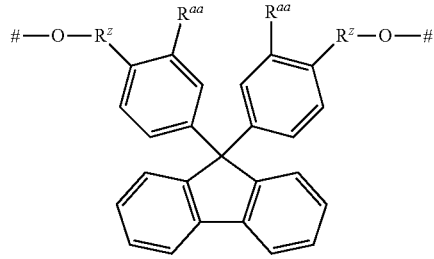
V-2

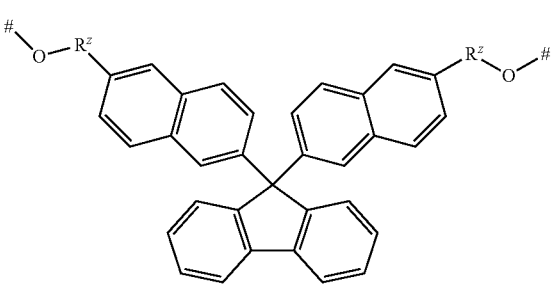
V-3

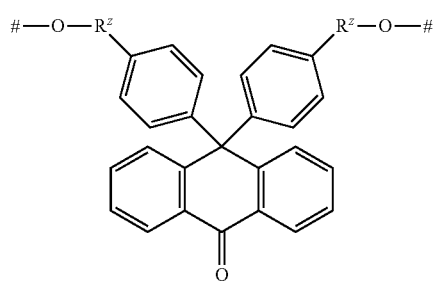
V-4

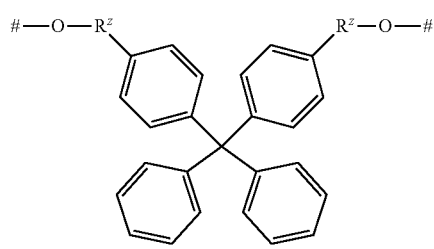
V-5

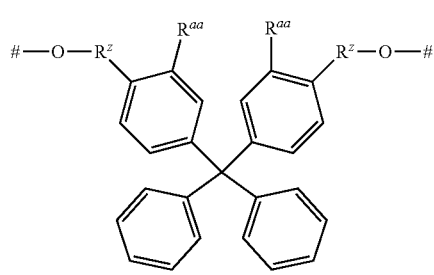
V-6

-continued
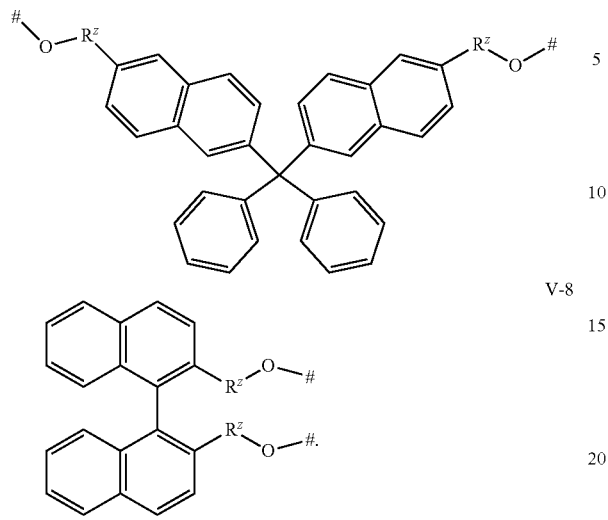
V-7
V-8
5. An optical device made of a thermoplastic resin as defined in claim 1.
6. The optical device of claim 5, wherein the optical device is an optical lens or an optical film.
* * * * *

UNITED STATES PATENT AND TRADEMARK OFFICE
CERTIFICATE OF CORRECTION

| | |
|---|---|
| PATENT NO. | : 11,760,712 B2 |
| APPLICATION NO. | : 16/968106 |
| DATED | : September 19, 2023 |
| INVENTOR(S) | : Karl Reuter et al. |

It is certified that error appears in the above-identified patent and that said Letters Patent is hereby corrected as shown below:

On the Title Page

Item (72) Inventor List, please delete "Shinya Ikeda, Tokyo" and insert -- Shinya Ikeda, Niigata -- therefor.

Signed and Sealed this
Fifth Day of March, 2024

Katherine Kelly Vidal
*Director of the United States Patent and Trademark Office*